US012708290B2

(12) United States Patent
Kim et al.

(10) Patent No.: US 12,708,290 B2
(45) Date of Patent: Aug. 18, 2026

(54) ASYMMETRICAL RHYTHMIC AUDITORY CUEING BASED GAIT MODIFICATION

(71) Applicant: University of South Florida, Tampa, FL (US)

(72) Inventors: Seok Hun Kim, Tampa, FL (US); Kyle Reed, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 1111 days.

(21) Appl. No.: 17/511,354

(22) Filed: Oct. 26, 2021

(65) Prior Publication Data

US 2022/0125336 A1 Apr. 28, 2022

Related U.S. Application Data

(60) Provisional application No. 63/105,761, filed on Oct. 26, 2020, provisional application No. 63/105,759, filed on Oct. 26, 2020.

(51) Int. Cl.
*A61B 5/11* (2006.01)
*A61B 5/00* (2006.01)
(Continued)

(52) U.S. Cl.
CPC ............ *A61B 5/112* (2013.01); *A61B 5/7405* (2013.01); *A63B 22/0292* (2015.10);
(Continued)

(58) Field of Classification Search
CPC ... A61B 5/112; A61B 5/7405; A63B 22/0292; A63B 71/0622; A63B 71/0686
See application file for complete search history.

(56) References Cited

U.S. PATENT DOCUMENTS 9,974,478 B1 * 5/2018 Brokaw ................. A61B 5/486
2006/0292533 A1 12/2006 Selod
(Continued)

FOREIGN PATENT DOCUMENTS

EP 3760120 A1 * 1/2021 ........... A61B 5/7455
JP 4686681 B2 * 5/2011 ............. A61B 5/112
(Continued)

OTHER PUBLICATIONS

Crosby, L., et al., "An Initial Investigation of the Responsiveness of Temporal Gait Asymmetry to Rhythmic Auditory Stimulation and the Relationship to Rhythm Ability Following Stroke", Front. Neurol., vol. 11, pp. 1-10 (Oct. 6, 2020). (Year: 2020).*
(Continued)

*Primary Examiner* — Dmitry Suhol
*Assistant Examiner* — Alyssa N Brandley
(74) *Attorney, Agent, or Firm* — HUSCH BLACKWELL LLP

(57) ABSTRACT

A method, apparatus, or system for modifying and assessing gait asymmetry is disclosed. The method, apparatus, or system may include measuring a first baseline step time for a first leg of an individual and a second baseline step time for a second leg of the individual and determining a first target step time for the first leg and a second target step time for the second leg. The first target step time can be different from the second target step time. The method may further include generating a series of auditory cues comprising a first cue duration corresponding to the first target step time and a second cue duration corresponding to the second target step time for synchronizing the first baseline step time and the second baseline step time with the first target step time and the second target step time, respectively. Other aspects, embodiments, and features are also claimed and described.

26 Claims, 17 Drawing Sheets

(51) Int. Cl.

| | |
|---|---|
| ***A63B 22/02*** | (2006.01) |
| ***A63B 24/00*** | (2006.01) |
| ***A63B 71/06*** | (2006.01) |
| *A63B 22/00* | (2006.01) |

(52) U.S. Cl.

CPC ...... *A63B 24/0062* (2013.01); *A63B 71/0622* (2013.01); *A63B 71/0686* (2013.01); *A61B 2505/09* (2013.01); *A63B 2022/0094* (2013.01); *A63B 2024/0093* (2013.01); *A63B 2071/0625* (2013.01); *A63B 2214/00* (2020.08); *A63B 2220/22* (2013.01); *A63B 2220/24* (2013.01); *A63B 2220/52* (2013.01); *A63B 2220/62* (2013.01); *A63B 2220/803* (2013.01); *A63B 2220/807* (2013.01)

(56) References Cited

U.S. PATENT DOCUMENTS

| | | | | |
|---|---|---|---|---|
| 2011/0184225 | A1* | 7/2011 | Whitall | A61B 5/112 600/28 |
| 2012/0059432 | A1* | 3/2012 | Emborg | A61N 1/36034 607/49 |
| 2017/0258370 | A1 | 9/2017 | Plotnik-Peleg | |
| 2018/0289287 | A1* | 10/2018 | Sio | G16H 20/30 |
| 2023/0148957 | A1* | 5/2023 | Stevens | A61B 5/1038 600/592 |

FOREIGN PATENT DOCUMENTS

| | | | | |
|---|---|---|---|---|
| WO | WO-2021001354 A1 * | 1/2021 | | A61B 5/112 |
| WO | WO-2021079127 A1 * | 4/2021 | | A61B 5/112 |

OTHER PUBLICATIONS

Dalla Bella, S., et al., "Individualization of music-based rhythmic auditory cueing in Parkinson's disease", Ann. N.Y. Acad. Sci., vol. 1423, pp. 308-317 (Jun. 4, 2018). (Year: 2018).*

Afzal, M., et al.; "A Portable Gait Asymmetry Rehabilitation System for Individuals with Stroke Using a Vibrotactile Feedback"; BioMed Research International, vol. 2015.

Bank, PJM, et al. "Comparing the efficacy of metronome beeps and stepping stones to adjust gait: steps to follow!." Experimental brain research 209.2 (2011): 159-169.

Ghai, S. "Effects of real-time (sonification) and rhythmic auditory stimuli on recovering arm function post stroke: a systematic review and meta-analysis." Frontiers in neurology 9 (2018): 488.

Hurt, C. P., et al. "Rhythmic auditory stimulation in gait training for patients with traumatic brain injury." Journal of music therapy 35.4 (1998): 228-241.

Kim, S. J., et al. "Changes in gait patterns with rhythmic auditory stimulation in adults with cerebral palsy." NeuroRehabilitation 29.3 (2011): 233-241.

Nascimento, L. R., et al. "Walking training with cueing of cadence improves walking speed and stride length after stroke more than walking training alone: a systematic review." Journal of physiotherapy 61.1 (2015): 10-15.

Pau, M., et al. "Effects of physical rehabilitation integrated with rhythmic auditory stimulation on spatio-temporal and kinematic parameters of gait in Parkinson's disease." Frontiers in neurology 7 (2016): 126.

Pelton, T., et al.; "Hemiparetic Stepping to the Beat: Asymmetric Response to Metronome Phase Shift During Treadmill Gait". Neurorehabilitation and Neural Repair, 24(5); 2010; pp. 428-434.

Ploughman, M., et al. "Therapists' cues influence lower limb muscle activation and kinematics during gait training in subacute stroke." Disability and rehabilitation 40.26 (2018): 3156-3163.

Shahraki, M., et al. "Effect of rhythmic auditory stimulation on gait kinematic parameters of patients with multiple sclerosis." Journal of medicine and life 10.1 (2017): 33.

Thaut, M. H., et al. "Rhythmic auditor y stimulation improves gait more than NDT/Bobath training in near-ambulatory patients early poststroke: a single-blind, randomized trial." Neurorehabilitation and neural repair 21.5 (2007): 455-459.

Yang, L., et al.; "Utilization of a lower extremity ambulatory feedback system to reduce gait asymmetry in transtibial amputation gait"; Gait and Posture, 36(3); 2012, pp. 631-634.

Yoo, G. E. et al. "Rhythmic auditory cueing in motor rehabilitation for stroke patients: systematic review and meta-analysis." Journal of Music Therapy 53.2 (2016): 149-177.

* cited by examiner

ASYMMETRICAL RHYTHMIC AUDITORY CUEING BASED GAIT MODIFICATION

CROSS REFERENCE TO RELATED APPLICATION

This application claims the benefit of U.S. Provisional Patent Application Ser. No. 63/105,761, filed Oct. 26, 2020, and U.S. Provisional Patent Application Ser. No. 63/105,759 filed Oct. 26, 2020, the disclosures of each of which are hereby incorporated by reference in their entirety, including any figures, tables, or drawings.

STATEMENT OF GOVERNMENT SUPPORT

N/A

TECHNICAL FIELD

The present disclosure relates, generally, to modifying the gait of a subject. More specifically, it relates to gait modification by utilizing asymmetrical rhythmic auditory cueing to dictate a desired gait of a subject.

BACKGROUND

Walking is fundamental to independence, and improving walking function is the goal most frequently voiced by stroke survivors. Despite this, only 7-22% of people with a stroke are able to regain sufficient function to be considered independent community ambulators. Also, people suffering from conditions affecting lower limbs experience diminished abilities to walk or to maintain a consistent gait. For example, people living with a partial or complete loss of a lower limb experience limited abilities to walk and run. There is, therefore, a significant need to improve systems and methods of improving the gaits of individuals with diminished abilities to walk or to maintain a consistent gait.

SUMMARY

The following presents a simplified summary of one or more aspects of the present disclosure, in order to provide a basic understanding of such aspects. This summary is not an extensive overview of all contemplated features of the disclosure, and is intended neither to identify key or critical elements of all aspects of the disclosure nor to delineate the scope of any or all aspects of the disclosure. Its sole purpose is to present some concepts of one or more aspects of the disclosure in a simplified form as a prelude to the more detailed description that is presented later.

In one example, a method, apparatus, or system for modifying and assessing gait asymmetry is disclosed. The method, apparatus, or system may include measuring a first baseline step time for a first leg of an individual and a second baseline step time for a second leg of the individual and determining a first target step time for the first leg and a second target step time for the second leg. The first baseline step time can be shorter than the second baseline step time. The first target step time can be different from the second target step time. The method may further include generating a series of auditory cues comprising a first cue duration corresponding to the first target step time and a second cue duration corresponding to the second target step time for synchronizing the first baseline step time and the second baseline step time with the first target step time and the second target step time, respectively.

These and other aspects of the invention will become more fully understood upon a review of the detailed description, which follows. Other aspects, features, and embodiments of the present invention will become apparent to those of ordinary skill in the art, upon reviewing the following description of specific, exemplary embodiments of the present invention in conjunction with the accompanying figures. While features of the present invention may be discussed relative to certain embodiments and figures below, all embodiments of the present invention can include one or more of the advantageous features discussed herein. In other words, while one or more embodiments may be discussed as having certain advantageous features, one or more of such features may also be used in accordance with the various embodiments of the invention discussed herein. In similar fashion, while exemplary embodiments may be discussed below as device, system, or method embodiments it should be understood that such exemplary embodiments can be implemented in various devices, systems, and methods.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1A:
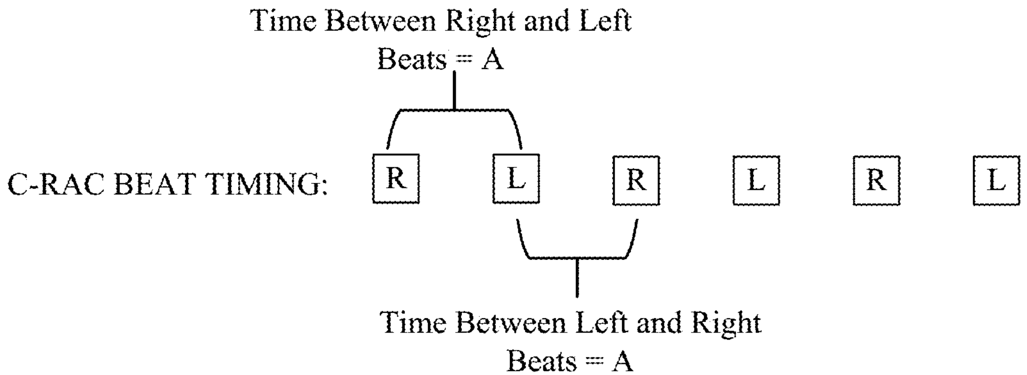
FIG. 1A shows sample beat timings for conventional RAC (C-RAC) and asymmetric rhythmic auditory cueing (A-RAC).
Figure 1A:
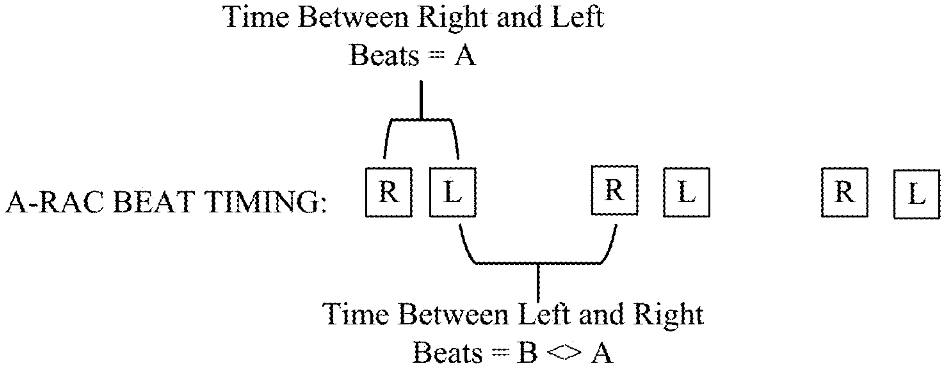

In the following detailed description, reference is made to the accompanying drawings, which form a part thereof and within which are shown by way of illustration specific embodiments of the present disclosure. It is to be understood that other embodiments may be utilized and structural changes may be made without departing from the scope of the present disclosure.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

Often, individuals suffering from conditions affecting lower limbs experience diminished abilities to walk or to maintain a consistent gait. For example, individuals living with a partial or complete loss of a lower limb (such as via an amputation) experience limited abilities to walk and run. Such individuals also experience increased risks of falling as a result of their conditions. According to studies, there were approximately 1.6 million individuals living with a loss of limb in the United States in 2005, with 65% of amputations involving lower limbs. Moreover, individuals suffering from debilitating impairments associated with, for example, Parkinson's disease, stroke, and cerebral palsy typically also suffer from gait impairments, thereby limiting their abilities to safely perform everyday activities, such as walking. These individuals consequently have increased susceptibility to injuries and falls as a result of their decreased mobility and steadiness while standing or walking. According to a study, approximately 800,000 individuals in the United States suffer a new or recurring stroke each year, with approximately 6 million individuals living with gait impairments caused by one or more strokes. A common disability associated with strokes is that of hemiparetic, or asymmetric, gait, with the problems associated with asymmetric gait being discussed below.

Accordingly, individuals with a lower limb amputation experience limited functional walking. Such individuals may regain some degree of independent ambulation by wearing a prosthesis. However, lower limb amputees' gait velocity is slower than that of healthy persons and their gait patterns are known to be inefficient compared to healthy subjects. Inefficiency of gait is more evident in those with transfemoral amputation than in those with transtibial amputation. People with unilateral transfemoral amputation (UTFA) demonstrate notable asymmetry in their gait pattern, e.g., longer step length and lengthened swing time of the prosthetic leg compared to the sound leg. Asymmetry of ground reaction force during walking is also observed, which is primarily due to the absence of knee extension and active push-off on the prosthetic side. Interestingly, gait asymmetries are present regardless of the type of prosthetic leg. The literature suggests that improvement of gait symmetry reduces energy expenditure, which suggests increasing gait symmetry is a major rehabilitation goal for people with amputation. The asymmetry of the gait pattern may result in altered muscle activities in the sound leg. For instance, more abnormal muscle activity and range of motion of the sound leg are reported in people with UTFA compared to the healthy controls. These results suggest that therapists may need to pay more attention to developing an efficient gait rehabilitation program for people with UTFA.

Decreased weight bearing on the prosthetic leg resulted in an abnormal gait pattern in people with UTFA. The altered gait pattern over-stresses the use of the sound leg during daily activities. The asymmetric weight distribution on the limbs may not only limit walking ability but also lead to secondary physical conditions in both the sound and prosthetic limbs. People with unilateral amputation commonly complain of hip and/or knee joint pain and osteoarthritis in the sound limb and experience osteoporosis in their amputated limb. Back pain is also commonly observed in people with lower limb amputation. This suggests that developing a proper weight distribution mechanism on the lower limbs might minimize or prevent these secondary physical conditions following amputation. Therefore, symmetry of weight loading during walking might be an important component of gait rehabilitation in people with UTFA.

Similarly, as discussed above, stroke patients suffer from impaired gaits, as well as individuals suffering from conditions associated with Parkinson's disease and other debilitating conditions and events. While such individuals often set a goal of regaining the ability to properly and safely walk, a minority of people (7-22%) are able to regain sufficient function to be considered independent community ambulators following a stroke. There is, therefore, a significant need to understand how to retrain gait to maximize gains in functional mobility post-stroke.

One example of a common gait impairment following stroke is hemiparetic (or asymmetric) gait, resembling a limp. Hemiparetic gait results from weakness and poor range of motion in the paretic (more affected) leg, limiting leg extension at the end of stance phase and is correlated with decreased walking speed, reduced walking efficiency, and increased susceptibility to injuries and falls. Since the paretic leg does not extend backward, the person can only take a small step forward with the non-paretic leg. People with a stroke may compensate with larger paretic-side steps, leading to step length asymmetry, a key feature of hemiparetic gait. There has been a recent surge of interest in investigating rehabilitation approaches that fix this "problem" of gait asymmetry post-stroke, yet it is not clear if gait symmetry is ideal or even achievable for a person with a stroke who has two limbs with fundamentally asymmetric properties.

Outcomes of gait rehabilitation can be quantified as changes in walking function (e.g., how well can a person walk from one place to another) or walking quality (e.g., how well-coordinated is the walking pattern). A common measure of walking function is walking velocity. Walking velocity is indicative of overall gait performance and can differentiate levels of disability. A velocity of 0.8 m/s is often considered the minimum threshold for community ambulation, and people who are able to ambulate in a shopping center have a mean gait speed of 1.14 m/s. A common measure of walking quality is gait symmetry. A normal gait tends to be symmetric in kinematics and dynamics and has a 4-6% difference in vertical force and temporal parameters between the two legs. Gait often becomes asymmetric (or 'hemiparetic') as a consequence of a unilateral stroke affecting leg motor areas. Hemiparetic gait is characterized by significant asymmetry in temporal (e.g. double-limb support time) and spatial (e.g. step length) measures of interlimb coordination. Propulsive force of the paretic limb is also reduced compared to the nonparetic limb, as are work and power of the paretic plantar flexors. Finally, vertical ground reaction forces (GRFs) are decreased on the paretic limb relative to the nonparetic limb, reflecting diminished weight bearing by the paretic limb.

One issue that must be considered is that people with hemiparesis due to stroke have different force and motion capabilities on each leg. The paretic leg is weaker and has a more limited range of motion than the non-paretic leg. Rehabilitation science has not advanced to the point where these problems can be fully corrected. Therefore, when retraining walking post-stroke, the system is an inherently asymmetric system. From a biomechanical view, two physically different systems (i.e., legs) can only have the same motion if the forces controlling them or the forces resulting from the movement are different. Therefore, it is likely that restoring kinematic symmetry will be at the expense of kinetic symmetry, or vice versa. Indeed, when an individual with an asymmetric impairment walks with symmetric step lengths, other aspects of gait become asymmetric, such as the forces in the joints, the amount of time standing on each leg, and other temporal variables, all of which can be detrimental to efficiency and long-term viability. Understanding how symmetry affects function could change the fundamental nature of clinical gait rehabilitation. The results from this research could also help tailor rehabilitation treatment to target each person's specific impairment.

Accordingly, what is needed are improved systems and methods of improving the gaits of individuals with limited functional walking capabilities. While certain aspects of conventional technologies have been discussed to facilitate the present disclosure, Applicant in no way disclaims these technical aspects, and it is contemplated that the disclosed embodiments may encompass one or more of the conventional technical aspects discussed herein.

The present disclosure may address one or more of the problems and deficiencies of the prior art discussed above. However, it is contemplated that the present disclosure may prove useful in addressing other problems and deficiencies in a number of technical areas. Therefore, embodiments in accordance with the present disclosure should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, otherwise constitutes prior art under the applicable statutory provisions, or is known to be relevant to an attempt to solve any problem with which this specification is concerned.

The present disclosure includes systems and methods of improving a gait of an individual by utilizing rhythmic auditory cueing (RAC), particularly asymmetric rhythmic auditory cueing (A-RAC), and particularly methods of improving gaits of individuals suffering from conditions that limit their ability to safely and efficiently walk. In various embodiments, beats (in auditory cueing) can be manipulated asymmetrically so that a gait of an individual can move closer to having a symmetrical walking pattern (which obtains improved results over conventional RAC methods). Exemplary methods involve the generation and application of signals at varying time gaps to provide asymmetrical cues for an individual to take a step in tune with the auditory signals. By utilizing asymmetrical cues, the methods can be applied to individuals having asymmetrical gaits, such as from suffering an amputation or stroke, to improve their asymmetrical gaits and alter the gaits to be more symmetrical

1.1. General Concepts

In various implementations, RAC can be used to facilitate a more symmetric gait pattern using an audible cue, such as, e.g., a cue created by a metronome or a musical beat. It guides the individual to synchronize the audible cue with the time of foot contact during walking. Individuals with neurological disorders, such as Parkinson's disease, stroke, and cerebral palsy have improved symmetrical and functional walking following RAC training. However, although people with unilateral lower limb amputation, especially unilateral transfemoral amputation (UTFA), experience significant asymmetrical gait patterns in their daily activities, to our knowledge few studies have investigated the effect of RAC on gait symmetry in these population. In a preliminary study, healthy individuals could change their temporospatial gait symmetry after training with RAC. The results indicate that RAC can be utilized as an alternative training approach for people with UTFA.

Asymmetric rhythmic auditory cueing (A-RAC) involves applying beeps with different time gaps before each step indicating to the person when each foot should be placed, whereas symmetric rhythmic auditory cueing involves applying beeps with the same time gaps before each step. To illustrate, FIG. 1A shows sample beat timings for conventional RAC (C-RAC) and A-RAC. For C-RAC, the timing gaps between beats for left and right foot placements are the same, whereas for A-RAC the timing gaps between beats for left and right foot placements are different.

As mentioned above, symmetric rhythmic auditory cueing can be utilized for neurological rehabilitation. The present disclosure further demonstrates that an asymmetric version can provide different, yet in some cases more beneficial, outcomes. The mechanism of A-RAC is based on the principle that the gait timing is specified and the user aims to match that beat with their gait. This causes the person to change their gait pattern. The asymmetric version additionally affects the gait symmetry. A-RAC can be used to train a person with a gait asymmetry to walk more symmetrically. In one exemplary method, training can be performed by spacing the beeps closer together on the foot that typically steps with a longer step time. The beeps or other cues serve as a constant reminder to speed up the typically slow leg.

However, in an alternative method, training can be performed by extending the spacing or time between the beeps or cues on the foot that typically steps with a longer step time. By exaggerating the gait asymmetry during training in the direction of the leg with the longer step time, the resulting gait pattern during post-training may be reduced and made more symmetric. This after-effect may occur in the opposite direction and could correct the user's gait when the user is not listening to the audible cues. Correspondingly, to increase the step length, gait asymmetry can be exaggerated by reducing the spacing between the audible cues on the foot that typically steps with the shorter step time beyond a target step time for the leg with the shorter step time such that the resulting gait pattern during post-training may be increased in the direction of step length and made more symmetric.

In various embodiments, the audible cues may be adapted based on a user's current gait pattern. For example, in various embodiments, gait parameters characterizing a user's gait pattern, such as step length, step time, speed, stride length, stride time, etc., may be measured via wearable or non-wearable measurement instruments, such as sensors (position sensors, force sensors, motion sensors that may be attached to the lower extremities), cameras, accelerometers, gyroscopes, etc. (via a smartphone or other portable device). Thus, the current gait pattern of an individual can be compared with a target or desired gait pattern and the audible beats or cues can be modified based on the results of the comparison. Accordingly, if an individual's gait pattern is close to the target gait pattern, then the audible cues may not be changed or may be slightly modified, whereas if the individual's current gait pattern is not close to the desired gait pattern, the audible cues may be modified, such as by increasing the tempo or adjusting the space/period in between beats, to attempt to improve the individual's gait pattern to being closer to the target/desired gait pattern.

In various embodiments, a feedback controller is integrated in a portable electronic device that provides the audible cues to the user, in which the feedback controller that measures gait parameters in real time and calculates changes in the audible cues will likely lead to a reduction in asymmetry and a balanced gait pattern. For example, in one embodiment, gait parameters will be continuously measured for a set period, such as one minute, but the controller will use an average of the last twenty seconds, as a non-limiting example, to calculate the changes for the next iteration.

In various embodiments, the portable electronic device can play audible cues continuously throughout an individual's walking activities. Alternatively, in some embodiments or modes of operation, the portable electronic device can be configured to intermittently play (and not play) the audible cues during the individual's walking activities. In this way, when the audible cues are being played, the individual can adapt his or her walking gait to correspond to the audible cues. Correspondingly, when the audible cues are not being played, the individual can try to train their brain to learn how to maintain the desired walking pattern without receiving audible cues. Then, when the audible cues are resumed, the audible cues may be adapted or fine-tuned to further adjust the individual's walking pattern based on feedback, as previously discussed, in some embodiments.

Rhythmic auditory cueing can only vary one parameter, the speed. A-RAC can also vary speed, but it can also vary the asymmetry, so the method is very well suited to training symmetry. Further, the amount of asymmetry can change throughout training, either on a session-by-session basis or in real time based on how they are walking. Thus, individuals with UTFA who suffer from asymmetrical walking would great benefit from A-RAC gait training.

1.2. Exemplary Preliminary Experiment

Figure 1B:
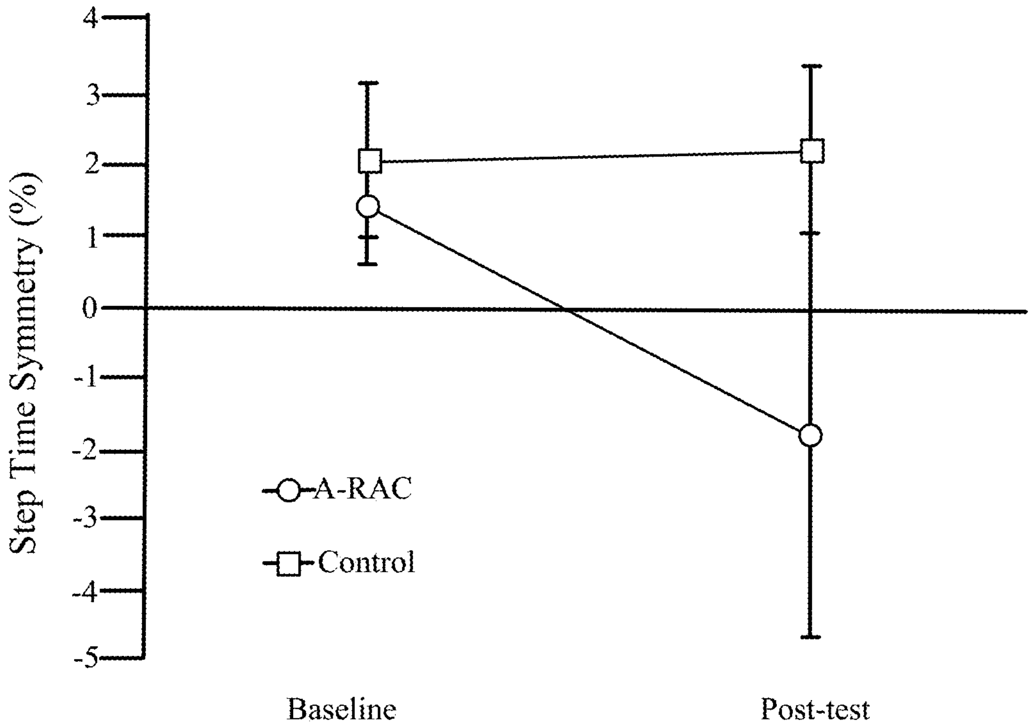
FIG. 1B is a graphical representation comparing baseline and post-test step time symmetry results from an exemplary asymmetric rhythmic auditory cueing (A-RAC) method in accordance with various embodiments of the present disclosure.

As shown in FIG. 1B, a preliminary experiment was performed to examine whether people who are neurologically intact can adapt a new gait pattern following A-RAC gait training. Six healthy young adults participated in this study and they were randomly divided into either the A-RAC group (n=3) or the control group (n=3). Subjects' temporospatial variables (e.g., step time and step length) were examined using the ProtoKinetics Zeno Walkway before training (baseline), immediately after training (post-test), and after a 5-minute over-ground walking (follow-up). The A-RAC group underwent a 30-minute gait training with asymmetrical auditory cueing. To apply a 2:1 ratio of A-RAC between the legs during training, an audio file was created using MATLAB® R2018b based on the baseline step time data and then uploaded into an examiner's mobile device. While turning on the asymmetrical auditory beats, the trainer walked behind the subject to ensure the subject was following the asymmetrical beats correctly. The control group did not have any gait training.

All three subjects in the A-RAC group showed noticeable changes in step time symmetry after gait training, but those in the control group did not (FIG. 1B). The mean change in step time symmetry was 3.2% in the A-RAC group and 0.17% in the control group at posttest. The amount of symmetry change after training in the A-RAC group was maintained to a certain extent at follow-up (1.9% difference from baseline). Two out of three subjects in the A-RAC group also showed clear changes in step length symmetry (1.3%) and 3.4% difference from baseline) following training and the changes were retained to a certain extent (2.1% and 2.2% difference from baseline, respectively) at follow-up. The results of the preliminary experiment showed that A-RAC gait training could modify gait symmetry in neurologically intact individuals. This suggests that gait training with A-RAC may have a high likelihood of succeeding for people with lower limb amputation.

1.3. Exemplary Gait Training Experiment

Another preliminary experiment was performed, in which the subjects underwent a total of 30 minutes of training. The training session consisted of three 10-minute bouts of over-ground walking with 2 minutes of rest between bouts. The experimental group had A-RAC during training and the control group received conventional RAC. The subjects carried an electronic device capable of emitting an auditory signal, and optionally electronically coupled to one or more earphones. The electronic device can execute a mobile application that calculates the duration of auditory cueing that is applied to each leg based on the subject's mean step time at the baseline test. The ratio of auditory cueing between the sound and prosthetic legs is determined relative to the baseline step time, such that the ratio of auditory cueing is customizable or adjustable based on measured stepping metrics from individual subjects. In an embodiment, a 2:1 ratio of A-RAC between the sound and prosthetic legs, respectively, was used for the experimental group. Since the prosthetic leg usually takes more prolonged steps than the sound leg, the training paradigm focuses on decreasing step time of the prosthetic leg and increasing step time of the sound leg. For example, if the mean step time at baseline is 600 milliseconds (msec), the duration of auditory cueing for the sound side is $$800 \text{ msec } \left(600 \times \frac{4}{3}\right)$$

and that for the prosthetic side is $$400 \text{ msec } \left(600 \times \frac{2}{3}\right),$$

yielding the desired 2:1 ratio of the sound leg to the prosthetic side. However, if necessary, the ratio of auditory cueing can be adjusted prior to training. The control group received a symmetrical ratio (1:1) of RAC during the group's gait training.

1.3.1. Example 1

Similar to the Preliminary Examination described above, in another experiment, eleven healthy young adults were randomly divided into three groups: an A-RAC group, a conventional RAC group, and a control group. The subjects' spatiotemporal variables (such as step time and step length) were assessed at a comfortable walking gait before training (i.e., baseline), after training (i.e., post-test), and after a five-minute over-ground walking period (i.e., follow-up). For training, each subject in each of the groups underwent a 30-minute gait training, consisting of three bouts of over-ground walking (10 minutes per bout) with a two-minute break between each bout. The A-RAC and conventional RAC groups received asymmetrical (2:1 ratio) and symmetrical (1:1) audio cueing, respectively, for gait training. The control group listened to a series of three different beats (slow, moderate, or fast) of musical arrangements during gait training. To apply the rhythmic auditory beats between the legs during training, audio files were created based on each subject's baseline step time data.

Symmetry indices for each subject were calculated using the following equation:

$$\text{Symmetry Index } (SI) = \frac{(\text{right} - \text{left})}{0.5(\text{right} + \text{left})} \times 100$$

A positive value indicates a greater step time or a longer step length on the right side. A zero value represents a perfect symmetry between the right and left legs.

The paired t test was conducted to examine changes in spatiotemporal gait symmetry across three testing periods. The independent t test was used to assess gait symmetry differences between the A-RAC and control groups. The conventional RAC group was not included in the statistical analysis due to a limited sample size in the example.

Figure 2A:
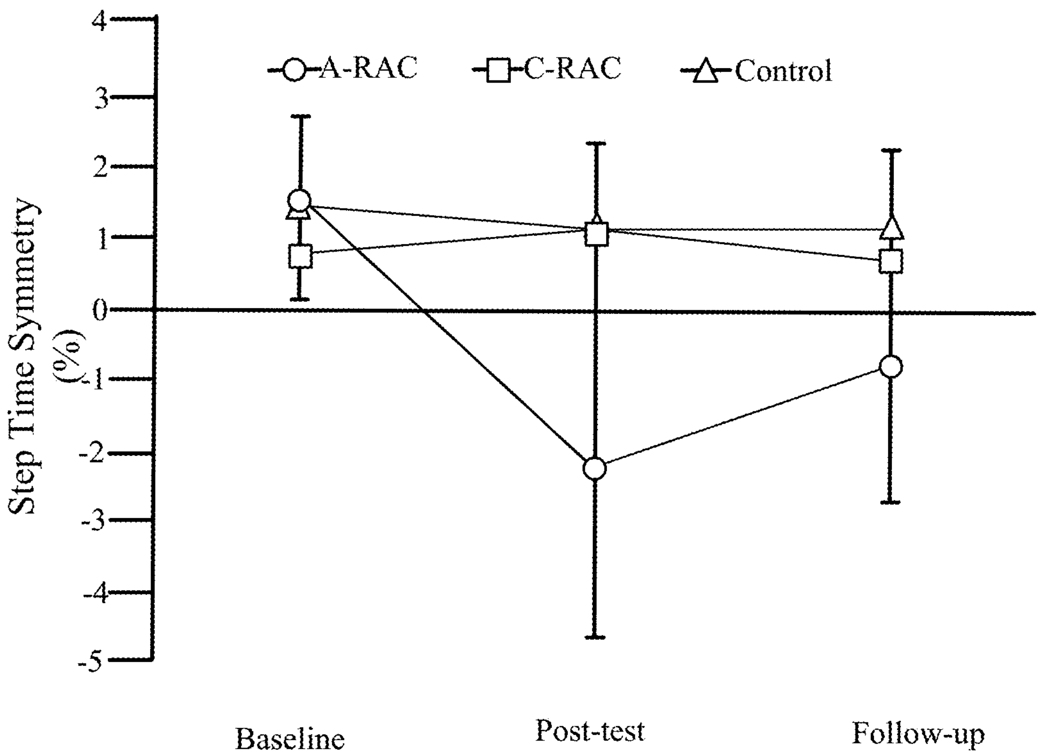
FIG. 2A is a graphical representation comparing step time symmetries across baseline, post-test, and follow-up periods for an A-RAC group, a conventional RAC (C-RAC) group, and a control group. A zero value represents perfect symmetry, and error bars represent standard deviations.
Figure 2B:
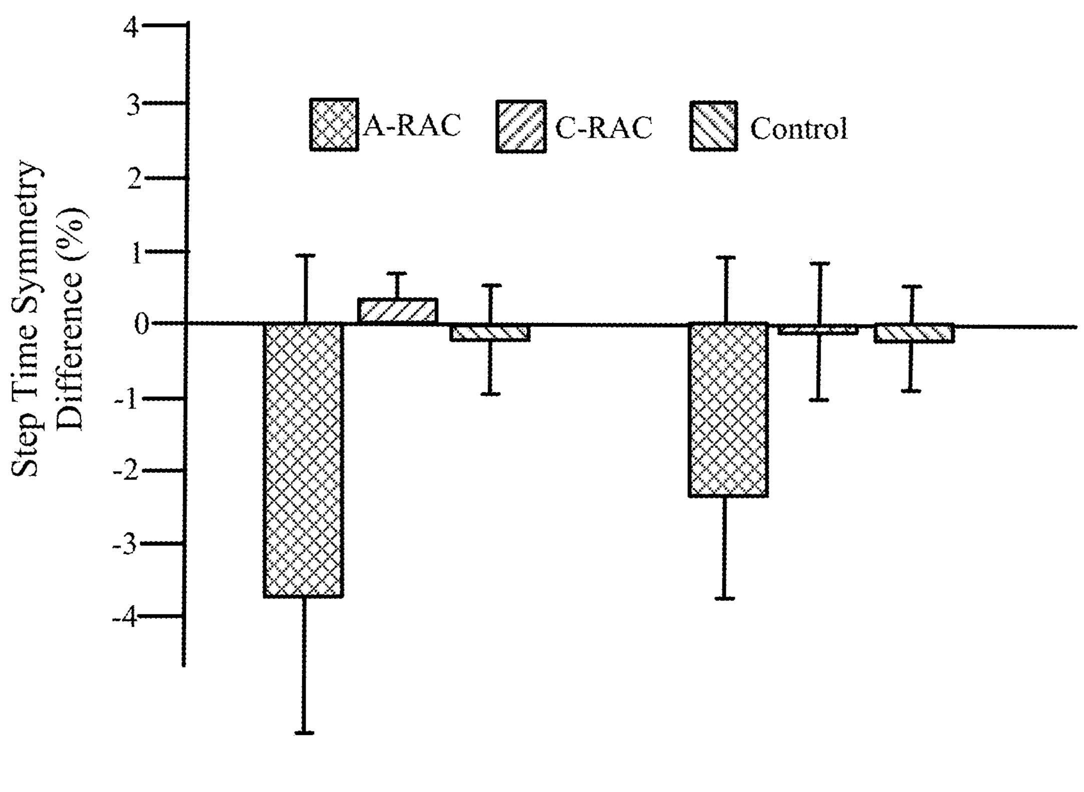
FIG. 2B is a graphical representation comparing step time symmetry difference percentages across post-test and baseline, as well as between follow-up and baseline, periods for an A-RAC group, a conventional RAC group, and a control group. Error bars represent standard deviations.

As shown in FIGS. 2A and 2B, the A-RAC group showed significant changes in step time symmetry at post-test recordings (3.71%) difference from baseline, $p<0.05$). The amount of change in step time symmetry was maintained at follow-up (2.28% difference from baseline, $p<0.05$). However, step time symmetry changes in the convention RAC and control groups after training were negligible (0.33% and 0.19% differences from baseline, respectively). Changes in step time symmetry between the A-RAC and control group were significantly different at post-test ($p<0.01$) and at follow-up ($p<0.05$).

Figure 3A:
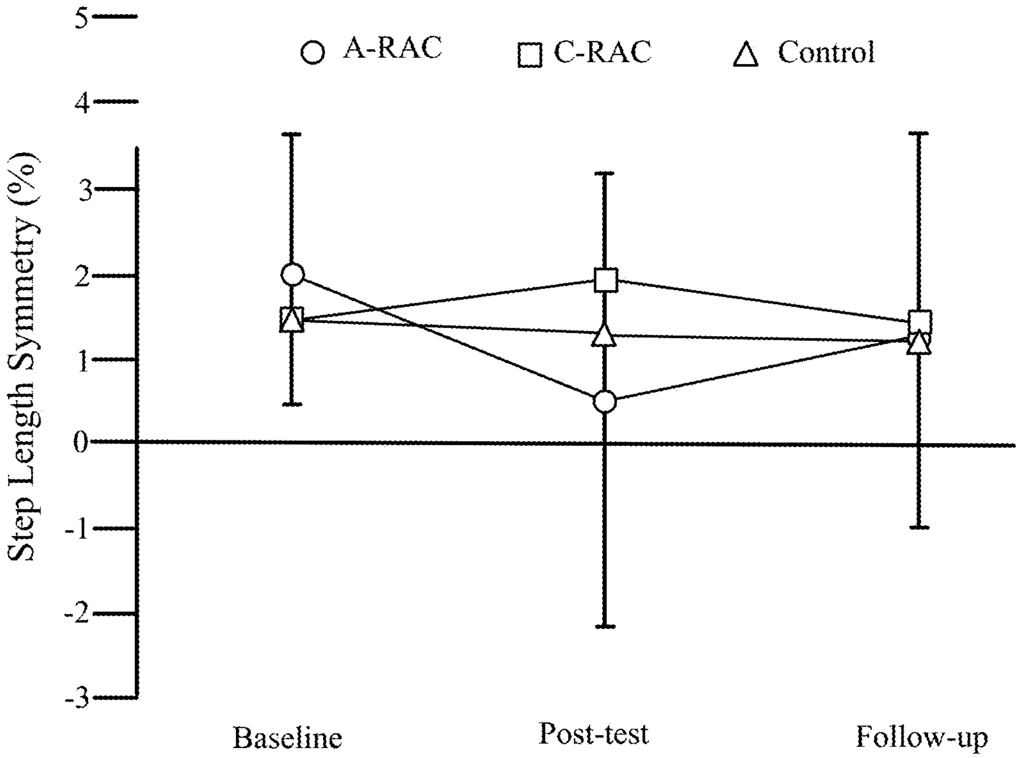
FIG. 3A is a graphical representation comparing step length symmetries across baseline, post-test, and follow-up periods for an A-RAC group, a conventional RAC group, and a control group. A zero value represents perfect symmetry, and error bars represent standard deviations.
Figure 3B:
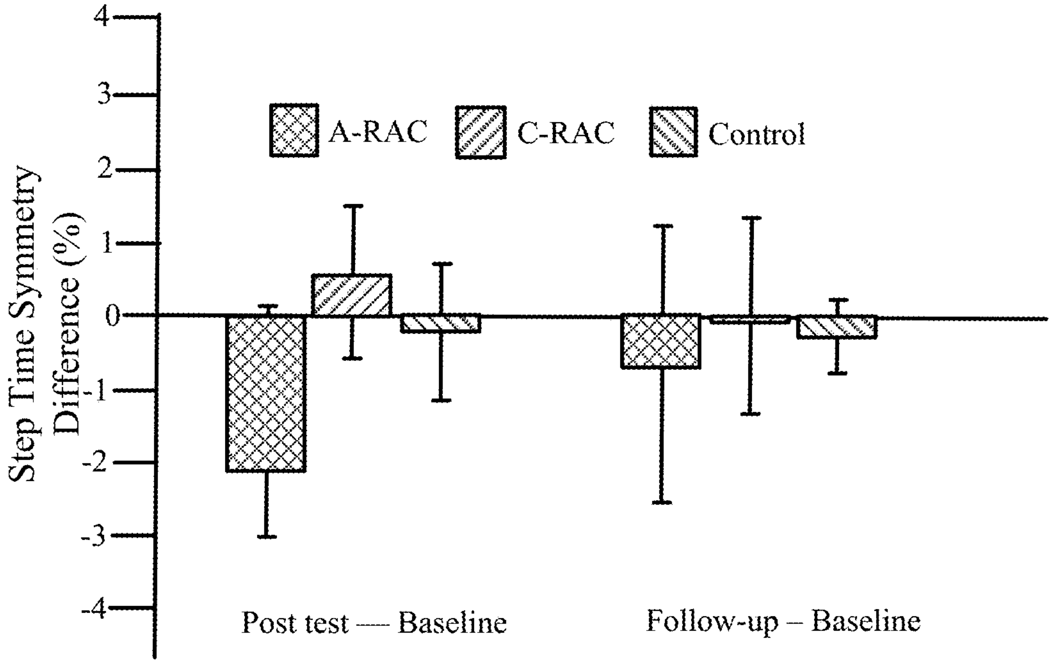
FIG. 3B is a graphical representation comparing step length symmetry difference percentages across post-test and baseline, as well as between follow-up and baseline, for an A-RAC group, a conventional RAC group, and a control group. Error bars represent standard deviations.

As shown in FIGS. 3A and 3B, none of the groups showed significant changes in step length symmetry after training. However, change in step length symmetry in the A-RAC group, was noticeably greater (1.51% difference from baseline) than that in the conventional RAC (0.51% from baseline) and control groups (0.22% from baseline).

The results of the experiment showed that A-RAC gait training can modify gait symmetry in healthy individuals, thereby suggesting that the A-RAC training has a high likelihood of succeeding for individuals with asymmetrical gait patterns.

2. Examples of Two Simultaneous Therapy Interventions Systems and Methods

2.1. General Concepts

This section further discusses systems and methods using two simultaneous perturbations: treadmill training and auditory cueing with symmetric or asymmetric ratios between legs. The two simultaneous interventions are discussed above in connection with Section 1.1.3. The disclosure below shows that combinations of tied-belt treadmill training and symmetric rhythmic auditory cueing (RAC) enhance gait performance more than symmetric RAC overground. In addition, combinations of split-belt treadmill training and asymmetric rhythmic auditory cueing (ARAC) further enhance gait performance.

The treadmill walking enforces adjusted speed to the user. Inadequate walking speed is a major contributing factor for inefficient gait among stroke survivors. When matching speed on a treadmill, the spatiotemporal differences between post-stroke and healthy matched subjects were reduced. While tied-belt treadmill walking (same speed on both sides) is able to improve walking speed (and increase efficiency as a result), it is not effective in improving gait symmetry long-term. Exaggerating asymmetry of an impaired gait (error augmentation) using a split-belt training (SBT) has shown a better post-training aftereffect. This aftereffect can be linked to the compensation mechanism in gait that is applied and stored through proprioceptors (sensory receptors within the muscles) during training. For instance, a person is driving a car with misaligned wheels pulling the car slightly toward the left. The person needs to constantly adjust the steering wheel to compensate for the tilted wheels to stay in a straight line. After a while, if the person drives a new car, the person will notice errors in steering the wheels toward the right when trying to go straight even though your new car is perfectly aligned. This is the effect of error augmentation training, and it is used for augmenting the asymmetry in stroke survivors with the goal of achieving reversed aftereffect (symmetric gait) post-training. While using an SBT has improved gait speed and interleg parameters such as step length, it does not show any aftereffect on intraleg parameters such as stride duration. It is possible that the lack of sensory feedback during training may account for the limited effects. In addition, accessing an SBT is not easy and most patients require visits to rehabilitation facilities for training. Another major challenge of this type of training is transferring the adapted patterns of SBT to overground walking and into the everyday home environment.

Rhythmic Auditory Cueing (RAC) is a training approach for gait symmetry that can affect a different range of gait parameters with a different impact than SBT. There is a strong connection between auditory feedback and the motor control system throughout the central nervous system (CNS). When a subject is walking, RAC influences them by providing musical rhythms to cue motor function. Research has tested the effect of RAC with various features, ranging from isochronic to biologically varied and from metronomes to music-based beats. Previous research has used RAC in which the cues to the left and right are the same duration. A preliminary study evaluates the effectiveness of Asymmetric Rhythmic Auditory Cueing (ARAC) in which the cue duration differs between the left and right legs. The adaptation of each leg has been shown to be independent of the other side. Therefore, it is hypothesized that ARAC is able to train each leg to their cue duration independently. Auditory cueing is more accessible than SBT and can be easily used in any environment (like home) through any sound playing device. However, the effectiveness of auditory cueing varies among patients depending on their rhythmic skills. While some patients have shown significant positive results, others show no or negative results.

Rehabilitation therapies using a single intervention (such as auditory cueing or treadmill training alone) are not capable of creating widespread gait changes that are effective for various patients who demonstrate different aspects of asymmetric gait. The combination of rehabilitation therapies shows better results than a single rehabilitation therapy, giving more ability to control parameter changes and the gait outcome performance as a result. Multiple-rehabilitation therapy includes two or more interventions applied simultaneously with the purpose of enhancing performance by engaging more sensory feedback and increasing the control over adjusting gait parameters. Single rehabilitation therapy can train gait to improve some parameters while making no change or worsening others. A multimodality approach can increase the outcomes of clinical training and focus on the individual's needs and capabilities. Combinations of tied-belt treadmill training and symmetric RAC show to enhance gait performance more than symmetric RAC overground.

Figure 4:
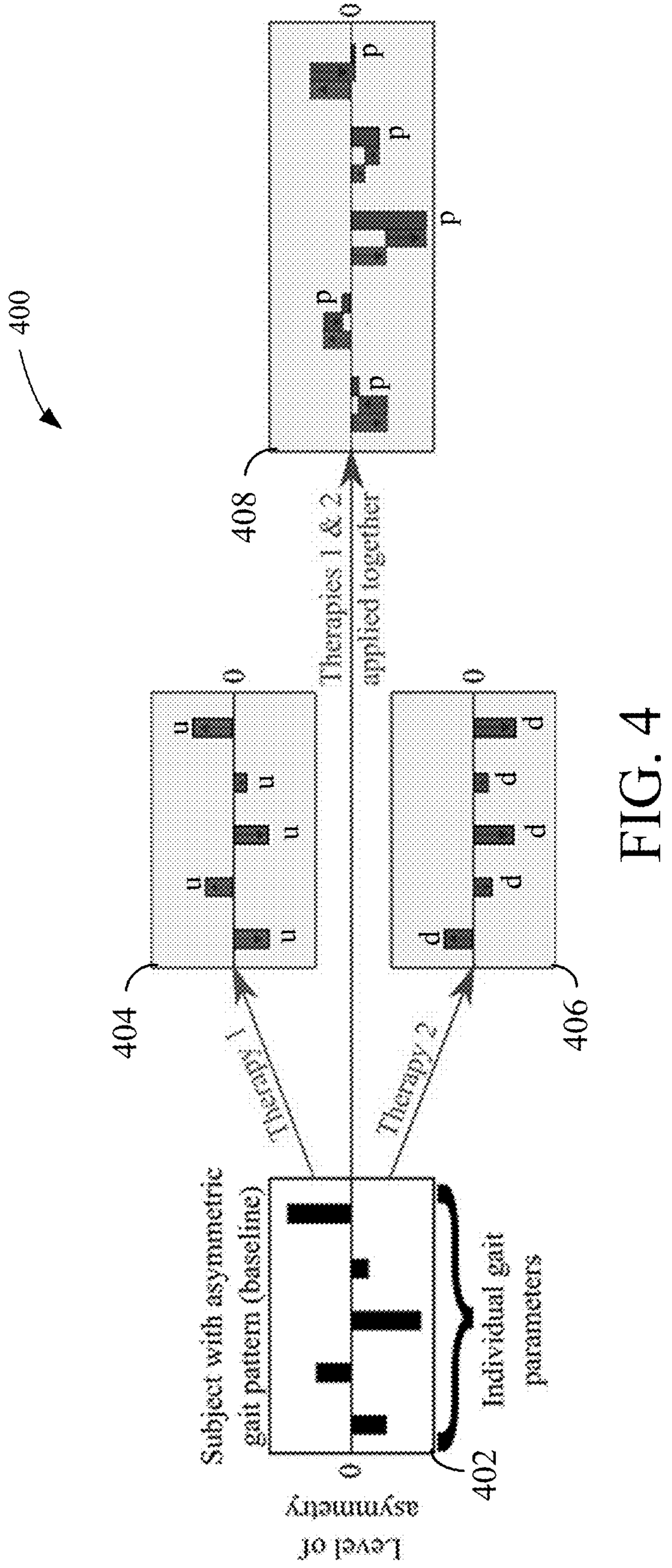
FIG. 4 shows the predicted behavior of the neuromusculoskeletal system by summing gait responses of two or more stimuli.

This section discloses the interworking of gait performance under two therapy interventions applied simultaneously: treadmill training and rhythmic cueing. It is hypothesized that the superposition principle applies to gait response; the net gait response caused by two or more stimuli (rehabilitation interventions) is the sum of the gait responses that would have been caused by each stimulus individually. FIG. 4 demonstrates the predicted behavior of the neuromusculoskeletal system under this hypothesis. Baseline rectangle 402 indicates different gait parameters level of asymmetry. Bars (u) in the upper rectangle 404 and bars (d) in the lower rectangle 406 indicate effects from two rehabilitation therapies (Therapy 1 and Therapy 2) applied separately. The rectangle 408 on the right is the hypothetical behavior of gait under multiple-rehabilitation therapy with therapies 1 and 2 applied simultaneously. Arrows indicate direction of asymmetric effect. Each parameter gets affected differently under different interventions (single rehabilitation therapy). Bars (p) summing arrows for corresponding parameters in the rectangle 408 on the right indicate estimated gait caused by simultaneous application of therapies 1 and 2. Thus, if multiple-rehabilitation therapy (combining two interventions) is applied, it is estimated that gait combines the response with a linear model.

2.1 Exemplary Methods

Rationale: To investigate the linearity of the gait response, one exemplary experiment evaluates two properties of linear systems: (1) additivity examines if the gait asymmetry under multiple-rehabilitation therapy is the sum of the gait asymmetries under single therapies, and (2) homogeneity evaluates if the proportion of asymmetries applied in each therapy are transferred. Evidence from existing research has given glimpses into the related walking mechanisms. Previous research has not yet studied the relationship between how gait responds under single and multiple-rehabilitation therapy.

The exemplary experiment shows that a combination of SBT and ARAC improves gait asymmetry of a person. Each method creates a type of asymmetry in the gait parameters. It is hypothesized Each of these therapies will affect the resulting gait independently of the other. Individual differences are considered between each subject and provide personalized models for the multiple-rehabilitation therapy that takes these differences into account to allow for future customization.

Figures 5A, 5B, 5C:
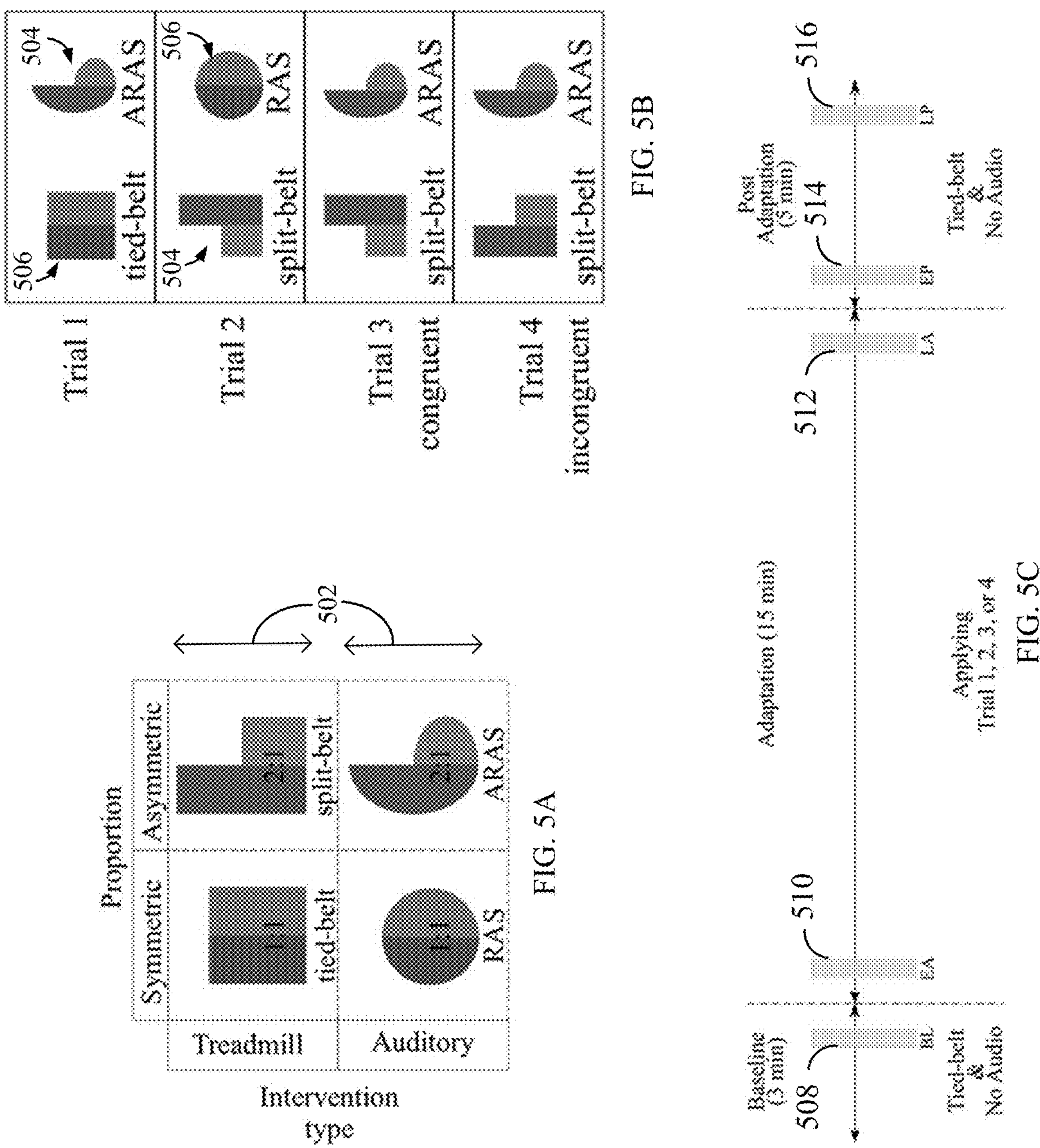
FIG. 5A shows examples of types of therapeutic interventions with symmetric and asymmetric proportions to the left and right legs.
FIG. 5B shows an example of an experimental design of four trials in an experiment.
FIG. 5C shows an example of a timeline of a duration of each section in the experiment.

Experimental design: A prospective cohort study is conducted to test the hypothesis. Each subject completed four different trials. Trials were at least 24 hours apart to make sure the residual effects from the previous trial had washed out. Multiple-rehabilitation therapy is applied by combining treadmill training and auditory cueing (FIG. 5A). FIG. 5A shows types of therapeutic interventions where height of each shape represents relative magnitude 502 of intervention. FIG. 5B shows the experimental design of each trial. Each trial incorporated one out of the four combinations depicted in FIG. 5B. For both asymmetric interventions, a 2 to 1 ratio is used between left and right. In trials 1 and 2, only one of the therapies has an asymmetric 2:1 pattern 504 while the other stayed symmetric 506. In trials 3 and 4, both therapies were applied with an asymmetric ratio of 2:1 in order to test the effect of the error augmentation mechanism. In trial 3, the asymmetric ratios were matched congruently where the faster belt was on the same side of the longer cue. In trial 4, the asymmetric ratios were matched incongruently, where the faster belt was on the same side of the shorter cue.

Participants: 16 healthy subjects (5 females; mean weight=70.5 kg, SD=13.0; mean height=170.9 cm, SD=9.6) with no prior history of gait impairment and no gait injury in the past 12 months form the final group. The subjects are divided into two equal groups of eight. Each completed all four trials (FIG. 5B) in random order. The side of the faster tread was switched in trial 2: left belt was faster for group A and the right belt was faster for group B.

Definitions, data collection, and procedure. Here, the term 'tied-belt' is used when the treadmill belts have the same speed, and 'split-belt' is used when each belt has a different speed. Percent asymmetry is defined as 'left-right' divided by the sum of left and right. This definition is chosen over 'slow-fast' because the side of asymmetry in the trials is considered. 5 time windows are calculated to compare the results of each trial. Each time window is the average of asymmetry between 25 left steps and 25 right steps (50 consecutive steps). Each subject took a few steps to adjust their walking after the start or stop of the training. Therefore, the time windows are located just after the first 10 steps or before the last 10 steps of each phase to make sure gait reaches stability (we first averaged the steps within each subject, then averaged the overall group). All experiments and data recording were conducted using the Computer Assisted Rehabilitation Environment (CAREN) system. CAREN system contains an immersive virtual reality environment, a 3D motion capture system, 6-degree-of-freedom motion base, instrumented dual-belt treadmill, and integrated force-plates. Reflective markers can be used on the lower body joints including metatarsal, heel, and lateral malleolus of the ankle to keep track of lower limb movements. Force-plates under the treadmill can capture ground reaction forces (GRF). Sound cues can be played through surround audio speakers mounted on the ceiling of the safety cage. Each cue can be the recorded standard dictionary (American English) pronunciation of the word 'right' or 'left'. Subjects were instructed to adjust each foot landing with their respective cue. Data were recorded at 100 Hz frequency. Prior to the first trial, subjects practiced on the tied-belt treadmill until they felt comfortable (approximately 3 minutes). During this time, they were asked to choose their comfortable speed while the operator changed the speed of the treadmill by increments of 0.1 m/s. Then the step time of the tied-belt walking was calculated by averaging 10 consecutive steps on the treadmill with the set comfortable speed. The fast belt was calculated by 4/3 of the comfortable speed, and the slow belt was half of the fast belt (2/3 of the comfortable speed) to keep the same average speed with a 2:1 ratio. The same process was implemented for the duration of asymmetric cues in ARAC. The cues are spaced isochronously based on the step time. For instance, if the average step time of a subject is 750 ms, a 2:1 ratio of ARAC has a 1000 ms cue on one side and a 500 ms cue on the other. Each trial took 23 minutes to complete (FIG. 5C) and had three phases: 3 minutes of baseline (tied-belt and no sound), 15 minutes of adaptation using one of the trials 1 through 4 combinations, and 5 minutes of post adaptation (tied-belt and no sound). FIG. 5C shows a duration of each section in the experiments. Rectangular shapes 1208, 510, 512, 514, 516 show the approximate location of time windows used for analysis. Each window includes 25 left and 25 right steps. The time windows are located after the first 10 steps or before the last 10 steps of each phase. Five time windows (BL baseline 508, EA early adaptation 510, LA late adaptation 512, EP early post-adaptation 514, and LP late post-adaptation 516) are measured in the experiment.

Data analysis: This experiment is a within-subject design. Multiple linear regression analysis can be conducted to test the hypothesis using two explanatory variables (trials 1 and 2) to estimate the outcome of two dependent variables (trials 3 and 4). Statistical analysis can be performed using IBM SPSS Statistics 26. The regression analysis reported the r-squared values, the significance levels using p value (0.05), and the collinearity diagnostics of the linear model. Each coefficient of the model was calculated based on 30 data points (2 trials 3 gait parameters 5 time windows).

2.2. Results

Figure 6A:
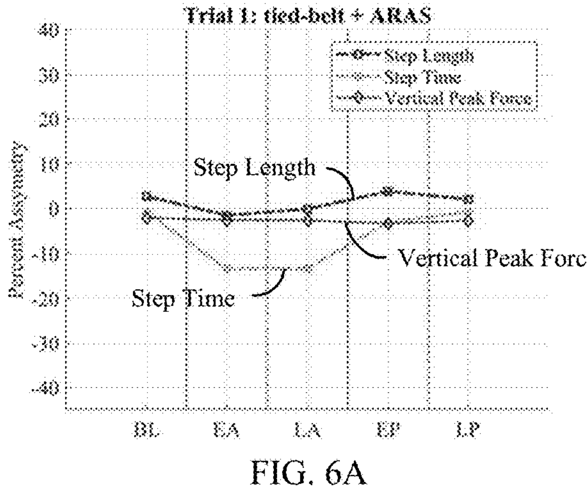
FIG. 6A shows percent asymmetry averages of step length, step time, and peak vertical force during five time-windows for trial 1.
Figure 6B:
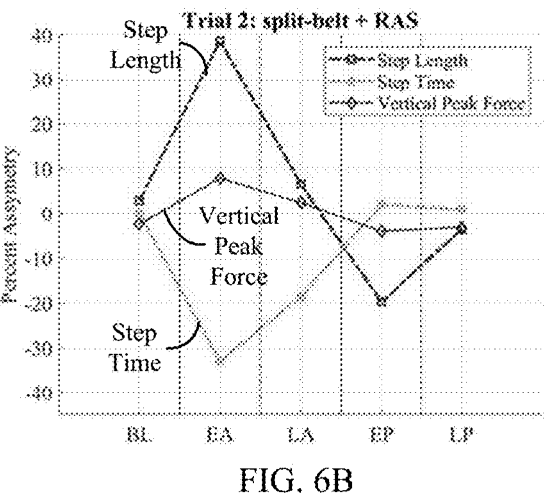
FIG. 6B shows percent asymmetry averages of step length, step time, and peak vertical force during five time-windows for trial 2.
Figure 6C:
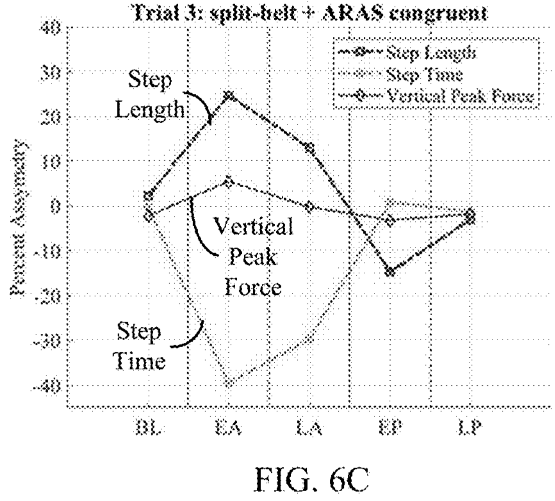
FIG. 6C shows percent asymmetry averages of step length, step time, and peak vertical force during five time-windows for trial 3.
Figure 6D:
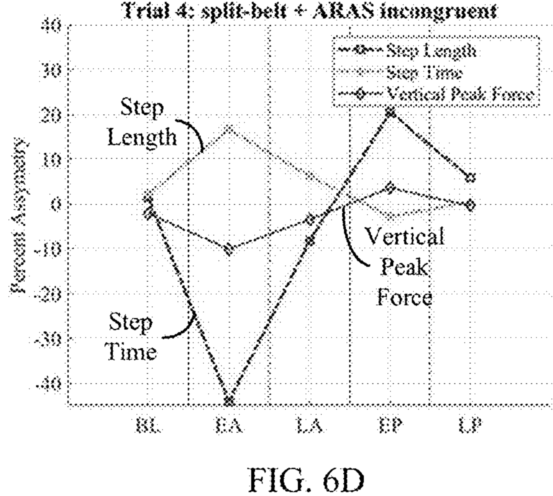
FIG. 6D shows percent asymmetry averages of step length, step time, and peak vertical force during five time-windows for trial 4.

Gait parameters: Subjects have an average comfortable speed of 0.91 m/s (SD=0.21) with average step time of 0.63 s (SD=0.093). Spatiotemporal parameters, as well as GRF, can be calculated. FIG. 6 indicates the average of percent asymmetry for step length, step time, and peak vertical force for group A during the three phases of the experiments (baseline, adaptation, post-adaptation). FIG. 6A shows trial 1 (tied-belt+ARAC) has a larger effect on step time compared to step length asymmetry. Auditory sensory feedback shows to influence largely the temporal parameters in the gait. Trial 2 (split-belt+RAC) in FIG. 6B affects both step length and step time (step length slightly more than step time). This result shows that SBT engages interlimb parameters. Trials 3 (congruent) and 4 (incongruent) use both SBT and ARAC effects at the same time. FIG. 6C with the congruent combination is indicating a sum effect of trials 1 (tied-belt+ARAC) and 2 (split-belt+RAC), while FIG. 6D with the incongruent combination is indicating the difference of trial 1 (tied-belt+ARAC) minus trial 2 (split-belt+RAC). In all SBT trials, there is an opposite change in asymmetry during early post-adaptation compared to early adaptation, which indicates the neural system has temporarily stored the applied asymmetry. Group B confirms the similar behavior of combined effect and storage of adaptation through overcorrection mechanism.

2.3. Linear Model

The superposition hypothesis proposes that the resultant change in gait under two stimuli is the linear combination of changes under each stimulus applied individually. To test the applicability of this hypothesis for gait response under asymmetric interventions, a linear model is developed for the three measurements (step length, step time, and peak vertical force) indicated in FIGS. 6A-6D. Two asymmetric stimuli, SBT and ARAC, are applied both individually and combined. Trial 1 and 2 include only one asymmetric stimulus, while trials 3 and 4 apply both stimuli asymmetrically. A model that estimates the gait response for the two later trials can be found based on the first two trials' gait responses. Equation 1 shows the linear model equations:

$$\mathrm{Trial3}_{estimate} = C_1 \times \mathrm{Trial1} + C_2 \times \mathrm{Trial2}$$

$$\mathrm{Trial4}_{estimate} = C_1 \times \mathrm{Trial1} - C_2 \times \mathrm{Trial2}$$

[Equation 1]

Figures 7A, 7B:
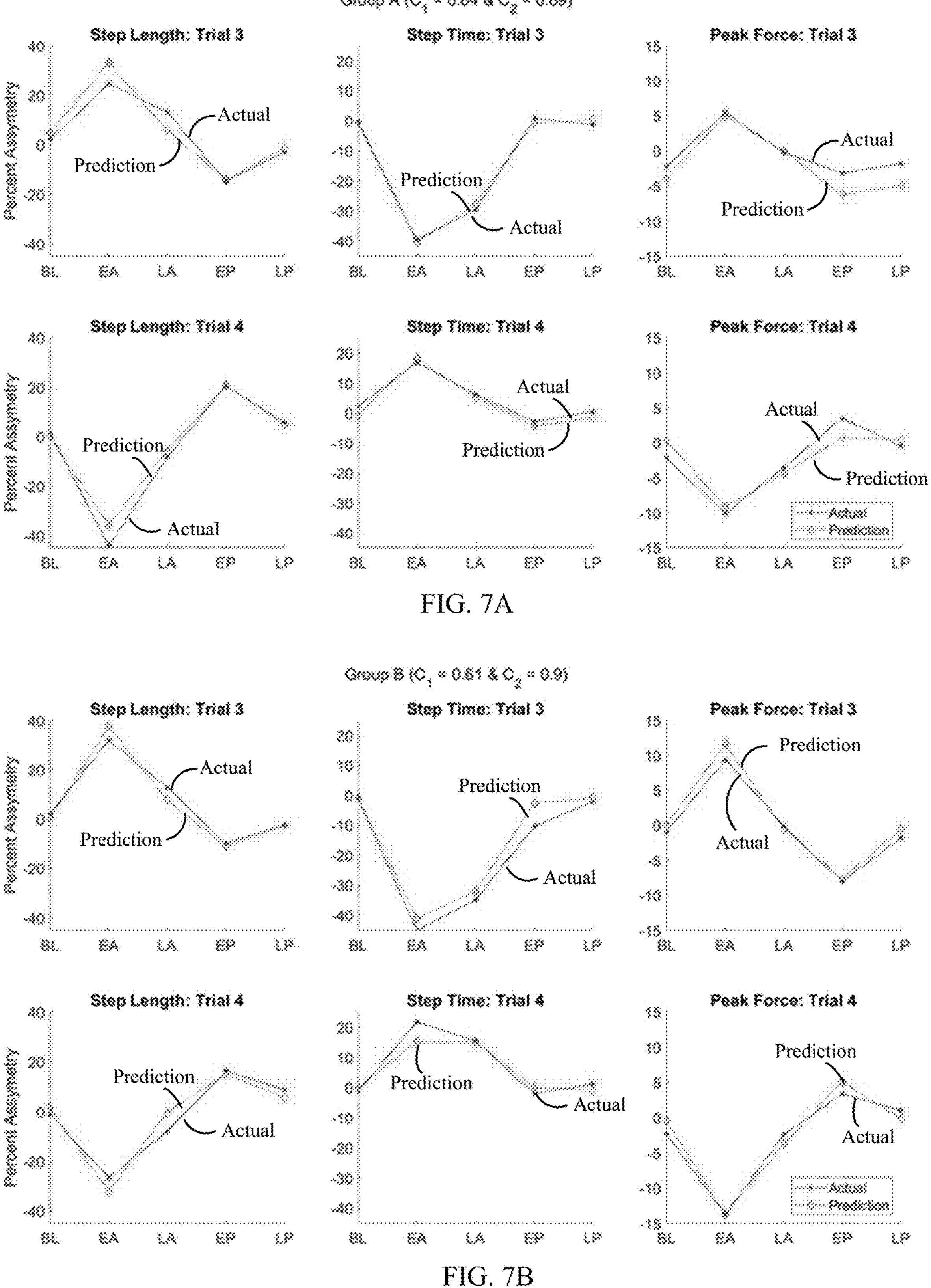
FIG. 7A shows an example of a linear model for a group having a coefficient value predicting the asymmetric performance of step length, step time, and peak vertical force compared to real data during trial 3 and 4.
FIG. 7B shows an example of a linear model for a group having a different coefficient value predicting the asymmetric performance of step length, step time, and peak vertical force compared to real data during trial 3 and 4.

$C_1$ and $C_2$ are constant coefficients of the model and stay the same in both equations because the interventions are applied with the same ratio in trial 3 and 4. The direction of applied asymmetry between trial 3 and 4 is changed to create the congruent and incongruent effect. The negative sign in trial 4 estimation indicates this difference. The two coefficients can be calculated by minimizing the root mean square error of the models at the same time. Trial 3 is the congruent combination because both directions of asymmetry in ARAC and SBT guide the gait toward the same asymmetric side. Trial 4 is the incongruent combination since the asymmetric direction of SBT and ARAC guide the gait toward opposite sides of asymmetry. The result of the fitted model is compared to the actual data (FIGS. 7A and 7B) for both groups A and B. This linear model estimates the behavior of three gait parameters in spatial, temporal, and kinetic areas over the three phases of the experiments for two combinations of asymmetric interventions.

[$C_1$, $C_2$] values are [0.84, 0.89] for group A and [0.61, 0.90] for group B. The overall r-squared values for group A and B models are 0.96 and 0.95, respectively. The r-squared values indicate the linear model explains more than 95% of variation within the data. The statistical test also calculates the p values of variables in the regression model. The p-values of both independent variables (trial 1 and trial 2) are 8.4e-20 in group A and 2.6e-19 in group B, indicating very strong evidence in favor of the hypothesis. The results show that combined asymmetric changes under trial 1 and 2 are significantly associated with changes in the response of trial 3 and 4. No collinearity is found among trials 1 and 2, having values of the variance inflation factor of 1 for all coefficients. While $C_2$ values in both groups are close (0.89 and 0.90), the $C_1$ value for group B is 0.61, indicating less effect of ARAC in group B compared to group A. After close examination, two subjects in group B showed close to zero or negative gait response under trial 1 (tied-belt+ARAC). Running the model for group B without the two outlier subjects gives values closer to group A: C1=0.77 and C2=1.00.

Figure 8:
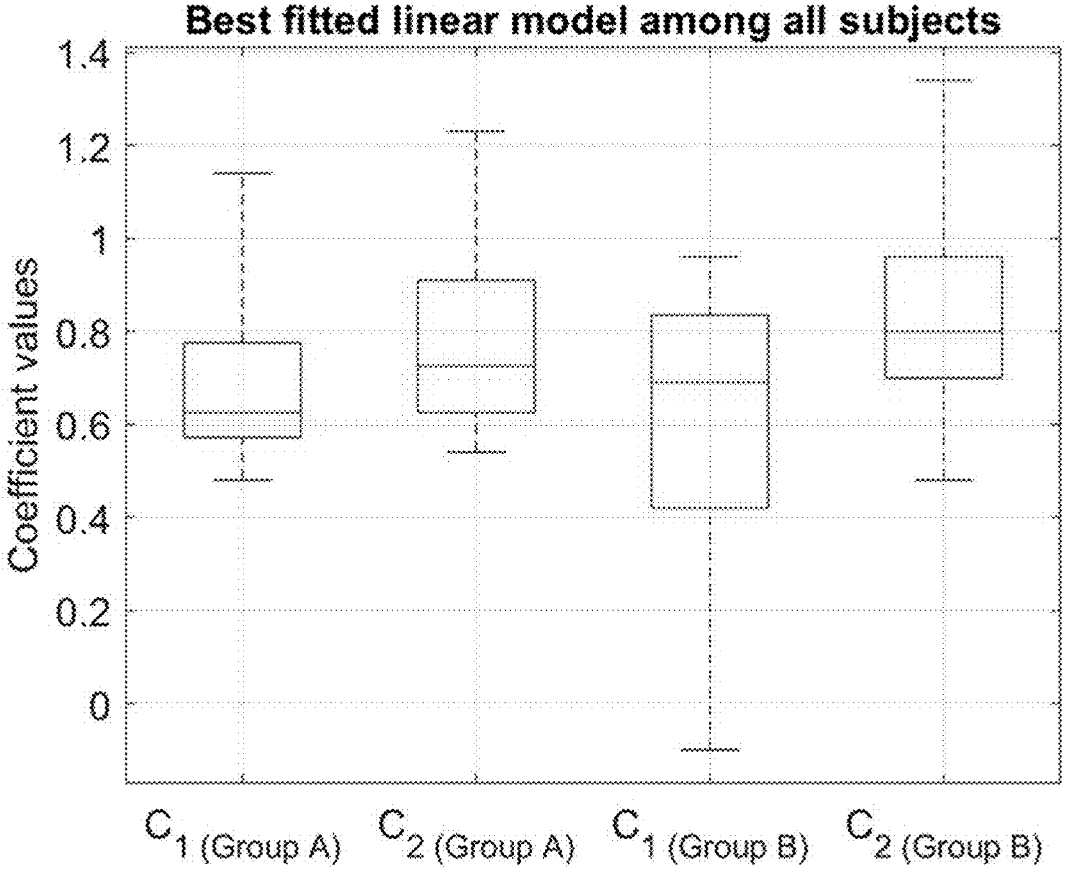
FIG. 8 shows an example of a whisker plot of coefficients for individual lineal models.

Personalized coefficients: The disclosed linear model of the gait response applies the superposition principle to asymmetric gait behavior under two simultaneous stimuli for the averaged results of all subjects. While the model presents a great fit for the averaged data supporting the hypothesis, it does not provide the optimal model for each individual. Thus, personalized coefficients are calculated for each subject by minimizing the root mean square error of the linear model (Equation. 1) for each person. FIG. 8 indicates the whisker plot of the coefficient values for the optimal personalized linear models. Two subjects in group B have close to zero or negative $C_1$ values for their best fit models. Training based on the auditory sensory feedback have shown none or even negative responses from participants depending on their rhythmic synchronization capabilities. As a result, the first quartile of $C_1$ in group B was stretched to near zero.

2.4 Discussion

Reciprocal movements such as walking contain three stages: initiation, cyclic pattern, and termination of the movement. CNS involvement has been suggested to vary between these stages. While initiation and termination are regulated at the supraspinal level, cyclic patterns are generated at the spinal level by central pattern generators (CPGs) and motor neurons. Therefore, the involvement of the supraspinal level in pattern generation is minimal and indirect. While there is strong direct evidence for the existence of CPGs in other vertebrates such as cats, there is indirect yet strong evidence supporting the existence of CPGs in humans. Moreover, research has shown that the brain does not control every detail of every movement. Instead, it only controls the endpoint, in this case, the final placement of the foot. It combines groups of muscles into modules for controlling tasks such as balance or walking. Modules simplify control of the coordination of movement by the nervous system and create flexibility within the muscles, sensory feedback, and neurons. In patients suffering from stroke, damage to the brain causes these modules to integrate together in order to make them easier to control. Therefore, the default walking module changes. The default walking module is the preferred walking style when no intervention is applied, whether a person has a healthy or an impaired gait. Now, due to the interconnections of the neuromusculoskeletal system, damage to the brain does not mean that the ability to walk normally and create new modules is completely lost. Cerebellar damage limits gait adaptation, but the capability for rehabilitation and gait retraining is retained after damage to the cerebral cortex. Therefore, stroke survivors with cerebral damage are capable of (re)learning symmetric walking patterns. (Re) training the muscles and restoring the pathways of neural control of movement through rehabilitation therapy have shown promising results. However, single rehabilitation therapy comes up short of complete gait restoration.

However, this disclosure shows that multiple rehabilitation therapies with different doses can improve gait restoration better than a single rehabilitation therapy. For example, two interventions are applied with 1:1 or 2:1 ratios at the same time in four different trials, measuring gait response each time. By combining two rehabilitation therapies, the superposition principle applies to the gait response under combined treadmill training and rhythmic cueing. Using the ARAC technique, an innovative method developed for the first time to match 2:1 asymmetry in split-belt with the same asymmetry in sound ratios. Auditory cueing (RAC or ARAC) has a feedforward mechanism where gait parameters adjust in anticipation of the upcoming cue. In this rehabilitation therapy, the ability to minimize the error between the predicted cue and the actual cue plays an essential role. Treadmill training (split-belt or tied-belt) has a feedback mechanism where the subject reacts to the change of speed or asymmetry, activating interleg control, which adjusts the gait parameters to bring the pattern back to the default walking pattern. While the treadmill trains gait by engaging muscles and proprioceptors into a different walking pattern, auditory cueing requires conscious attention to auditory sensory feedback.

Modeling gait response can lead to a better understanding of the neuromusculoskeletal system performance under multiple stimuli. A gait response model can also help with developing personalized multiple-rehabilitation therapies that encompass multitudinous aspects of individual capabilities. In this disclosure, a linear model is proposed for the gait response under simultaneous stimuli (interventions) and calculated the percentage of contribution of each stimulus to the final gait asymmetry in each subject. The coefficient values indicate the relative effectiveness of each intervention in the combined trials. A value of one for $C_1$ or $C_2$ indicates the full effect is realized. A coefficient between zero and one would indicate the effect of the intervention was partially transferred. $C_1$ and $C_2$ values for both groups are higher than 0.6 and less than 1, which indicates that less than 40% of the therapeutic effects of each intervention is lost when the therapies applied simultaneously. Three out of the four coefficients are higher than 0.84, meaning the loss of therapeutic effects of their corresponding interventions are 16% or less. For example, $C_1$=0.85 and $C_2$=0.91 for group A means that 85% of the ARAC effect and 91% of the SBT effect were demonstrated across step time, step length, and peak vertical force during combinations of ARAC and SBT. The high r-squared values and the level of significance confirmed that the suggested model estimates the gait response under two simultaneous stimuli with high accuracy.

While this model shows the average response of all subjects, it might not represent the best estimate for each subject individually. Rhythmic capability, muscle strength, physique, and other personal aspects can affect the gait response of individuals under asymmetric interventions. Level of impairment also change the effectiveness of different rehabilitation therapies between individuals. For this reason, it is important to look at the variability of the model among individuals. It is vital for the improvement of personalized therapies that individual characteristics, especially individual gait response to various inputs from different therapies, to be taken into consideration when prescribing a multiple-rehabilitation therapy.

Calculating personalized coefficients from gait responses of 16 healthy subjects showed more than 70% of the coefficient values are between 0.54 and 1, meaning that the majority of the healthy subjects demonstrated more than 50% of each individual intervention when combined. A coefficient of more than 1 for either $C_1$ or $C_2$ would mean adding an intervention has acted as a catalyst and emphasized the corresponding therapy method. A coefficient of zero (or close to zero) for either $C_1$ or $C_2$ would mean that the subject was not able to respond to the corresponding intervention or the effect of the corresponding intervention was lost completely or overlapped with the other intervention during the combined ARAC and SBT trials. Five subjects had a coefficient ranging between 1.06 and 1.34. This could indicate that the addition of a therapy method has made the other method more impactful. Two subjects indicated close to zero or negative coefficients during trial 1 (ARAC+tied-belt). This is not an unexpected outcome in therapies that are based on rhythmic auditory feedback. Previous research has shown that while some people have a positive response to rhythmic cueing, others might have none or even negative response. The performance of rhythmic cueing has been connected to the rhythmic skills of people.

If a minimum of 40% is considered as a considerable demonstration of asymmetries in gait response, more than 90% of the subjects are considerably affected from each intervention during both combined trials. While the exact coefficients for each subject might vary depending on their strengths and weaknesses, both the fitted linear model on the averaged data (FIGS. 14A and 14B) and the close range of the whisker plots for individuals (FIG. 15) indicate that neuromusculoskeletal system can linearly combine the effects of two simultaneous rehabilitation stimuli on gait asymmetric response. Experimental results showed that the additivity principle was met; however, the coefficients not being one indicates that the homogeneity was not fully applicable. Therefore, the superposition principle was largely applied. This result can lead to a better and improved combination of therapies that accommodate the needs of patients as well as leveraging their strengths for better outcomes.

This disclosure may have the potential to significantly impact gait rehabilitation in people with neuro-logical disorders such as stroke. Additional understanding is needed to get to this level, such as the development of accurate, reliable, and practical assessment methods to determine to what extent a patient responds to the individual or jointly applied sensory stimuli. Once the methods are ready to use, therapists can easily identify and apply optimal levels of sensory stimuli needed for personalized gait rehabilitation based on the patient's capabilities and needs. For example, a patient, who experiences significantly altered step time but minimally impaired step length after stroke, may require a great level of auditory cue and a minimal level of visual cue to maximize gait recovery. The linear regression model introduced in this study can help develop the methods that effectively assess the patient's responses to the sensory stimuli. This disclosure achieved two discoveries in the path of understanding gait response. First, ARAC is able to adapt different sides of gait by applying asymmetric cues with a 2:1 ratio, meaning that auditory sensory feedback can independently access each side of lower limbs. Second, gait response for these gait parameters can be mainly modeled as a linear system with the possibility of quantifying the contribution of various stimuli at the same time.

3. Examples of Asymmetric Rhythmic Auditory Cueing (A-RAC) Training Systems and Methods

3.1. General Concepts

Each year about 800,000 Americans suffer a new or recurrent stroke. The incidence of stroke is 0.82 per 1000 population in the world. In the United States, the rate is noticeably higher, with 2.9 per 1000 in the African-American population and 1.8 per 1000 in the Caucasian population. Most individuals following stroke are left with functional impairments that limit their activities of daily living. Patients may regain some degree of independent ambulation following rehabilitation. However, their walking ability (e.g., gait speed and endurance) decreases significantly, and their gait patterns become markedly altered compared to healthy subjects. The abnormal walking patterns increase risk of falls and co-morbidities such as osteoarthritis. Asymmetrical hemiplegic walking patterns that rely on their non-paretic leg are commonly observed in stroke patients. However, although researchers and clinicians have developed various types of therapeutic methods for recovery of gait after stroke, the methods have had limited successes in helping individuals regain gait symmetry and motor function in the lower limb. Therefore, a validated gait training program needs to be developed for effective recovery of gait in people with stroke. In this feasibility study, we will investigate the effects of a novel over-ground gait training using asymmetrical rhythms on gait symmetry and motor function of the lower limb in people with chronic stroke.

3.1.1. Asymmetric Gait Patterns in People with Stroke

People with stroke demonstrate notable asymmetry in their gait patterns. Although they improve spatiotemporal gait parameters over time, the gait asymmetry does not. Typical gait asymmetry of temporal variables includes lengthened swing time and shortened single limb support time of the paretic leg during walking, compared to the non-paretic leg. Stroke patients also show spatial gait asymmetry (e.g., longer step length) with their paretic leg. Asymmetrical weight bearing, usually measured with ground reaction forces (GRFs), between the paretic and non-paretic legs is commonly observed through the stance phase of walking. The GRF asymmetry is highly correlated with temporal variables (e.g., swing time and stance time) and motor recovery. Moreover, the literature indicates that gait asymmetry decreases the efficiency while walking and the improvement of gait symmetry reduces energy expenditure. The asymmetry of a gait pattern results in developing compensatory muscle activities in both the paretic and non-paretic legs following stroke. These outcomes suggest that developing an efficient gait training program, targeting gait symmetry is essential for the recovery of gait in people with stroke.

3.1.2. Diminished Motor Function in the Lower Limb Following Stroke

Motor impairments (e.g., muscle weakness, altered motor control, and abnormal tone) in the lower limb are commonly observed in people with stroke. These impairments cause the inadequate control of knee extensors and the absence of active push-off on the paretic side during walking. The altered muscle activities and motor control in both the paretic and non-paretic legs result in compensatory strategies for walking that relate to high risk of falls. The recovery of motor function in the lower extremity after stroke is also significantly related to independent ambulation. Fugl-Meyer Assessment of the lower extremity (FMA-LE) has been widely utilized to evaluate the recovery of LE motor function after stroke. The FMA-LE motor function score is correlated with walking speed and used as a predictor for the recovery of the LE motor function in people with stroke. Thus, in this section, the FMA-LE can be used as one of two primary measures to assess the recovery of motor function in stroke patients.

3.1.3. Gait Training for People with Stroke

Diverse therapeutic approaches can facilitate recovery of walking after stroke, such as: body-weight supported treadmill, robotic device, split-belt treadmill, rhythmic visual feedback, auditory cueing, functional electrical stimulation, and others. Body-weight supported treadmill training (BWSTT) is beneficial for gait rehabilitation in people with stroke and improves gait speed, endurance, and motor recovery of the lower limbs. Robot-assisted gait training (RAGT) can improve functional outcomes and walking ability, but the advantage of RAGT has not been consistent when compared to over-ground gait training. RAGT can improve balance control in individuals with stroke and can slightly change gait symmetry. However, the effects of BWSTT and RAGT are not superior to those of conventional therapies (e.g., over-ground gait training, Bobath training, and treadmill gait training) on spatiotemporal gait symmetry. Visual feedback during gait training reduces the risk of falls, increases anterior GRF, and improves control of body sway during gait. However, visual feedback is usually used by combining with other approaches, such as BWSTT and RAGT, and requires a computerized technology to display targets for the patients. Further, the effects of visual feedback on gait symmetry have been understudied. Split-belt treadmill training (SBTT) addresses gait symmetry directly by applying a different speed tread to each leg. SBTT can improve gait symmetry after stroke but the mechanism targets step length so it primarily affects spatial parameters. Moreover, about half of the stroke participants who underwent SBTT did not respond to this treatment. It is possible that the primary cause of gait asymmetry in the non-responders may be the alteration of other parameters such as a temporal variable. The gait training approaches mentioned above are mostly performed in a clinical setting. However, it is difficult for stroke patients to access the treatments mentioned above because few clinics provide gait training with these devices mostly due to cost. Moreover, since most falls in stroke patients occur during their daily activities like walking, gait training in the patient's home environment may better help them regain efficient walking patterns. Thus, there is a need to develop a more cost effective and accessible training method for people with stroke. Gait training using the proposed asymmetric rhythmic auditory cueing with adaptation can achieve this goal.

3.1.4. Gait Training with Rhythmic Auditory Cueing

Rhythmic auditory cueing (RAC) has been used in gait rehabilitation to facilitate recovery of walking using a consistently spaced audible cue created by a metronome or a musical beat. RAC guides the individual to synchronize the audible cue with the time of each foot's contact during walking. The literature shows that people with neurological disorders, such as Parkinson's disease and cerebral palsy improved functional and symmetrical walking following RAC training. Typically, symmetric RAC has been used to rehabilitate people with unilateral stroke, and its effects on gait symmetry is equivocal. An intensive gait training with RAC over 3 weeks is more effective than the neurodevelopmental treatment in promoting recovery of walking in people with subacute stroke. However, 6 weeks of RAC gait training was not superior to the conventional physical therapy in regaining gait symmetry. This limitation may be due to the symmetrical cueing which provides the same beats to both legs based on the patient's gait speed. Given a target walking speed, patients will count on the non-paretic side to follow the speed and rhythms. This may overstress the non-paretic side and lessen the use of the paretic side during training. The literature indicates that minimizing the use of the non-paretic side helps facilitate the learning of the paretic side. Accordingly, it is in need to develop gait training with auditory rhythms that reduces the use of the non-paretic side while increasing the use of the paretic side. As mentioned above, people after stroke commonly present increased step time with the paretic leg and decreased step time with the non-paretic side. Thus, it makes sense that using asymmetrical beats (e.g., applying a short beat to the paretic side and a prolonged beat to the non-paretic side) is an ideal gait training approach. This method would target both legs simultaneously and facilitates patients to learn more symmetrical and efficient walking patterns. No studies have investigated the effect of asymmetric rhythmic auditory cueing (A-RAC) on gait symmetry in people with stroke. In the preliminary study below, a stroke patient showed a significant improvement in their step time symmetry, increasing step time in the non-paretic leg and decreasing step time in the paretic leg after A-RAC gait training (see 3.3.1. Preliminary Study). Thus, the step time symmetry can be used as one of two primary measures for this study.

3.2. Exemplary Concepts

Given asymmetrical presentation in hemiparetic gait after stroke, i.e., increased and decreased step time with the paretic and non-paretic legs, respectively, it is logical that an intervention targeting both the paretic and non-paretic sides would be most effective in restoring symmetrical walking patterns. However, current gait training using auditory cueing has only focused on symmetric beats and its effect on symmetrical walking in stroke patients is inconclusive, especially when compared to conventional physical therapy. In fact, it is challenging for stroke patients to move the paretic foot to follow the symmetric beats, most likely due to impairments of motor control in the lower extremity. Maintaining the pace with consecutive symmetrical rhythms during walking may give an additional burden to stroke patients while practicing walking. Thus, the patients may only be able to keep pace with the cueing for limited steps. Asymmetric rhythmic auditory cueing (A-RAC) can apply auditory cues with different time gaps before each step indicating to the person when each foot should be placed. If the patients are trained with tolerated asymmetrical auditory cues between the legs that they can keep in time with, it might help them follow the cues more easily with their paretic leg and reduce the extra burden that they need to face during the walking task.

Figure 9:
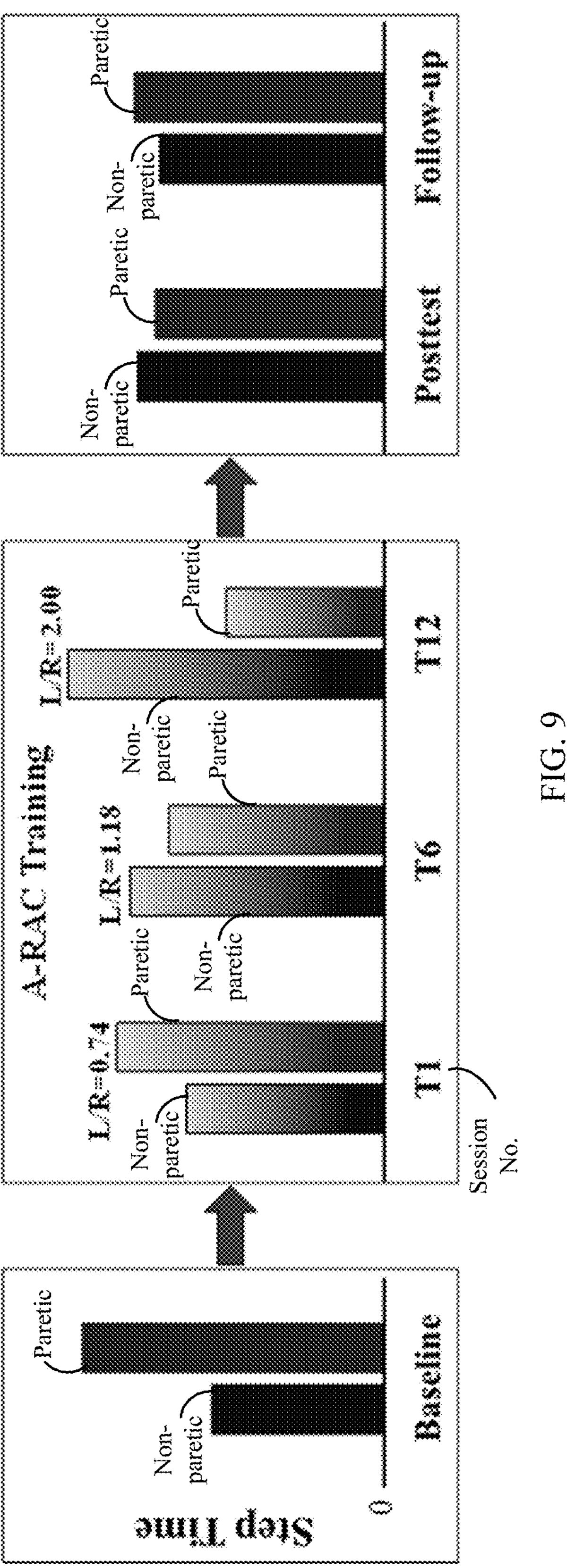
FIG. 9 shows a predicted model of gait training using asymmetric rhythmic auditory cueing (A-RAC) for the recovery of symmetrical walking in stroke patients.

The gait training with asymmetric auditory rhythms proposed in this feasibility study has not been demonstrated in the literature. The mechanism of A-RAC is based on the same principles as rhythmic auditory cueing in which the gait timing is specified, and the user aims to match that beat with their gait. This induces the person to change their gait pattern. The asymmetric version additionally affects the gait symmetry. A-RAC can be used to train a person with stroke to walk more symmetrically by directly targeting the asymmetrical patterns of gait. This would be done by spacing the beeps closer together on the foot that typically steps with a longer step time (i.e., paretic foot) and spacing farther on the foot that typically steps with a shorter step time (i.e., non-paretic foot). The beeps serve as a constant reminder to speed up the typically slow leg and slow down the typically fast leg. Symmetric RAC can only vary one parameter, the speed. A-RAC can vary speed and the asymmetry, so it is very well suited to training symmetrical walking. Manipulating the timing element (asymmetry) in addition to movement time (speed) during training may enhance rhythmic perception, affecting arousal and motivation, and facilitate the connections between auditory and motor pathways. Further, the amount of asymmetry can be modulated throughout training, either on a session-by-session basis or in real time based on how they are walking. In this proposed study, the degree of asymmetry will be adjusted for each training session based on the patient's tolerated asymmetrical rhythms (FIG. 9). FIG. 9 shows a predicted model of gait training using asymmetric rhythmic auditory cueing (A-RAC) for the recovery of symmetrical walking in stroke patients. Bars indicate step time of the non-paretic (left) and paretic (right) legs, respectively. The right and left will be switched if the non-paretic leg's step time is greater. The gradient bars represent A-RAC training sessions 1, 6, and 12 and the numeric values indicate the hypothetical ratios of asymmetric cueing between the legs during the training. Note that the ratios gradually increase across the training sessions, depending on the subject's progress. In the preliminary study, an individual with chronic stroke was compliant with the A-RAC gait training method and showed noticeable improvements of gait symmetry after a relatively short-term training (See 3.3.1. Preliminary Study). In addition, recovery of motor function in the lower extremity is critical to independent walking following stroke. However, whether auditory rhythms can improve motor function of the lower extremity has not been studied. The preliminary study below at section 3.3.1. revealed that a stroke patient who had A-RAC training improved his motor function of the lower extremity. Thus, individuals with stroke who suffer from asymmetrical walking may greatly benefit from A-RAC gait training. In this section, it is proposed to examine whether stroke patients who undergo gait training with A-RAC can improve symmetry of their gait patterns and motor function of the lower extremity, compared to gait training with symmetric rhythmic auditory cueing.

Studies have examined the changes in gait symmetry by manipulating a spatial variable (i.e., step length). However, the results of these studies revealed that humans are controlling spatial and temporal parameters independently through different neural circuits while adopting a new gait pattern. The limited response of stroke patients to the treatment approach (i.e., SBTT) suggests that some patients may respond to a different stimulation, like temporal variables, to improve their gait patterns. Moreover, the patient's adaptability to a change in each gait parameter after stroke may play an important role in adopting new gait patterns after stroke. So, further studies need to investigate whether a stroke patient's response to each treatment relates to the adaptability to a change in each parameter at baseline. Therefore, the proposed study compares the effect of training with an auditory rhythm on gait symmetry in individuals with high adaptability to A-RAC training to those with low adaptability. The results of this proposed study will help to develop an efficient gait training method to optimize walking recovery in people with stroke.

3.3. EXAMPLES

3.3.1. Exemplary Preliminary Study

Figure 10:
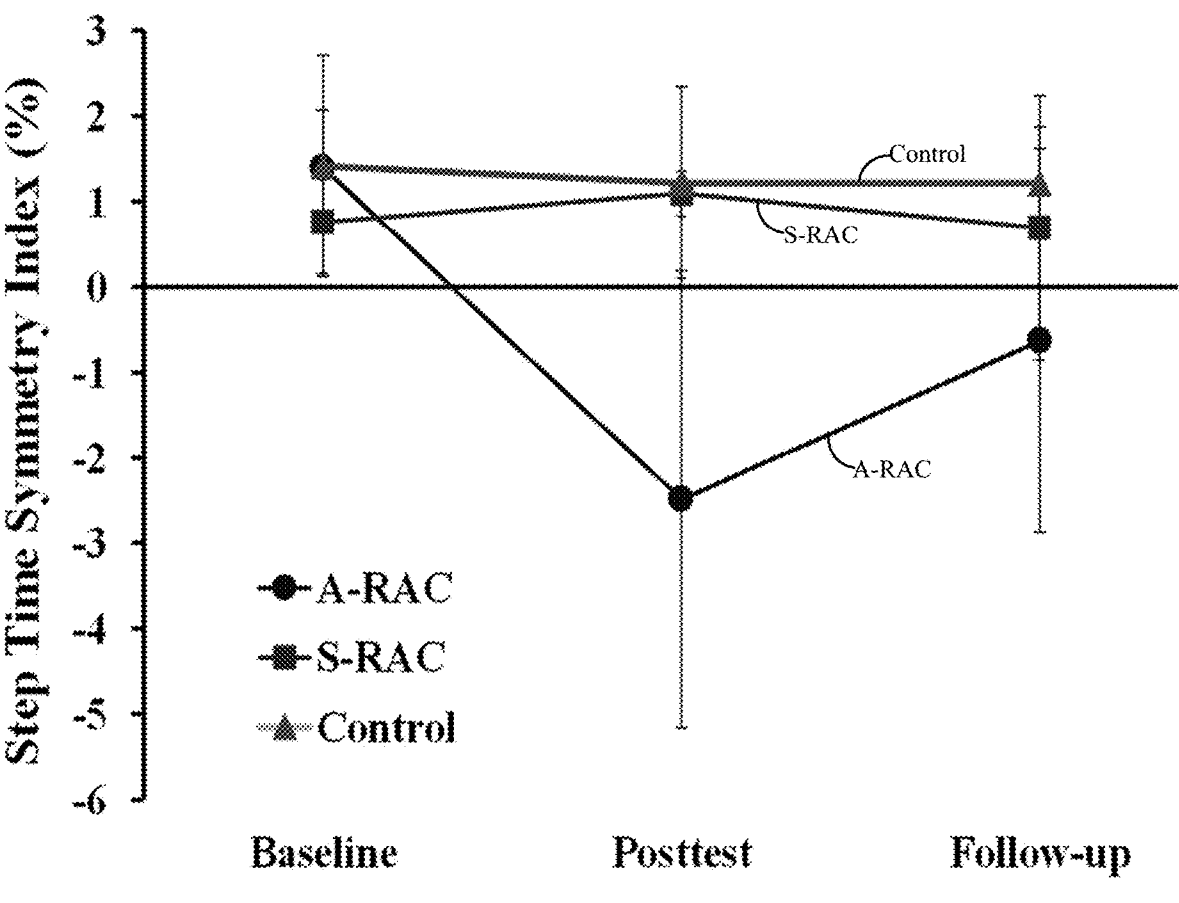
FIG. 10 shows changes in step time symmetry following gait training.

Two preliminary experiments were conducted to examine if A-RAC gait training could modify human gaits. In the first study, whether healthy individuals could adapt a new gait pattern following A-RAC gait training was investigated. Ten healthy young adults participated in this study, and they were randomly divided into three training groups: asymmetrical RAC (A-RAC, n=4), symmetrical RAC (S-RAC, n=2), and control (n=4). Subjects' step time was assessed using a gait analysis system before training (baseline), immediately after training (posttest), and after 5 minutes of over-ground walking (followup). In some examples, the gait analysis system may be the ProtoKinetics Zeno Walkway (ProtoKinetics, Havertown, PA). The A-RAC and S-RAC groups underwent a 30 minute gait training with asymmetrical (2:1 ratio) and symmetrical (1:1 ratio) auditory cueing, respectively. To apply the ratio of auditory cueing between the legs during training, an audio file including "Right" and "Left" sounds was created using a suitable software based on the baseline step time data and then uploaded into an examiner's phone. In some example, the software may be MATLAB R2020b (the MathWorks, Inc., MA). While turning on the auditory beats, the examiner walked behind the subject to make sure the subject was following the beats correctly. The control group listened to a series of three different beats (slow, moderate, or fast) from songs during gait training. The step time symmetry was assessed by calculating a symmetry index (SI) based on the following equation: SI (%)=[(right−left)/(0.5*(right+left))]*100 [60]. The right and left was switched if the left leg's step time was greater. The Wilcoxon Signed Rank test showed that the A-RAC group had statistically significant changes in step time symmetry after gait training ($p<0.05$), but the control group did not (FIG. 10). FIG. 10 shows changes in step time symmetry following gait training. Error bars represent standard deviations. Here, A-RAC indicates asymmetrical rhythmic auditory cueing, S-RAC indicates symmetrical rhythmic auditory cueing, and Control indicates normal walking. The Mann Whitney U test revealed a significant difference between the two groups ($p<0.05$). The mean change in step time symmetry was 3.88% in the A-RAC group and 0.19% in the control group at posttest. The amount of symmetry change after training in the A-RAC group was maintained at follow-up (2.02% difference from baseline). Although the S-RAC was not included for data analysis due to a small sample size, the changes in step time symmetry after S-RAC training were markedly less than those in the A-RAC group.

In the second study, whether A-RAC gait training could improve gait symmetry in a person (70-year-old male) with chronic stroke was examined. At baseline, the subject's step time of the non-paretic leg (0.85 sec) was markedly shorter than that of the paretic leg (1.46 sec). His baseline step time symmetry ratio (non-paretic/paretic) was 0.58. Prior to each gait training session, an adaptability test was performed to identify how much step time asymmetry the subject could acclimate to. The adaptability test included a 5-minute baseline audio file including "Right" and "Left" sounds asymmetrical step time ratio gradually changed from 0.58 to 2.0. The subject was asked to walk comfortably, following the music beats accurately. The results of the subject's adaptability test showed that he could adapt to a step time symmetry ratio of 0.92, 1.32, 1.45, and 1.57 prior to the first, second, third, and fourth session of training, respectively. Auditory cueing for each A-RAC training session was created using a suitable software and was based on the subject's baseline adaptability ratio. In some examples, the software is MATLAB R2020b. The procedures of the adaptability test and A-RAC training will be thoroughly described in 3.3.3. Testing Procedure.

Figure 11:
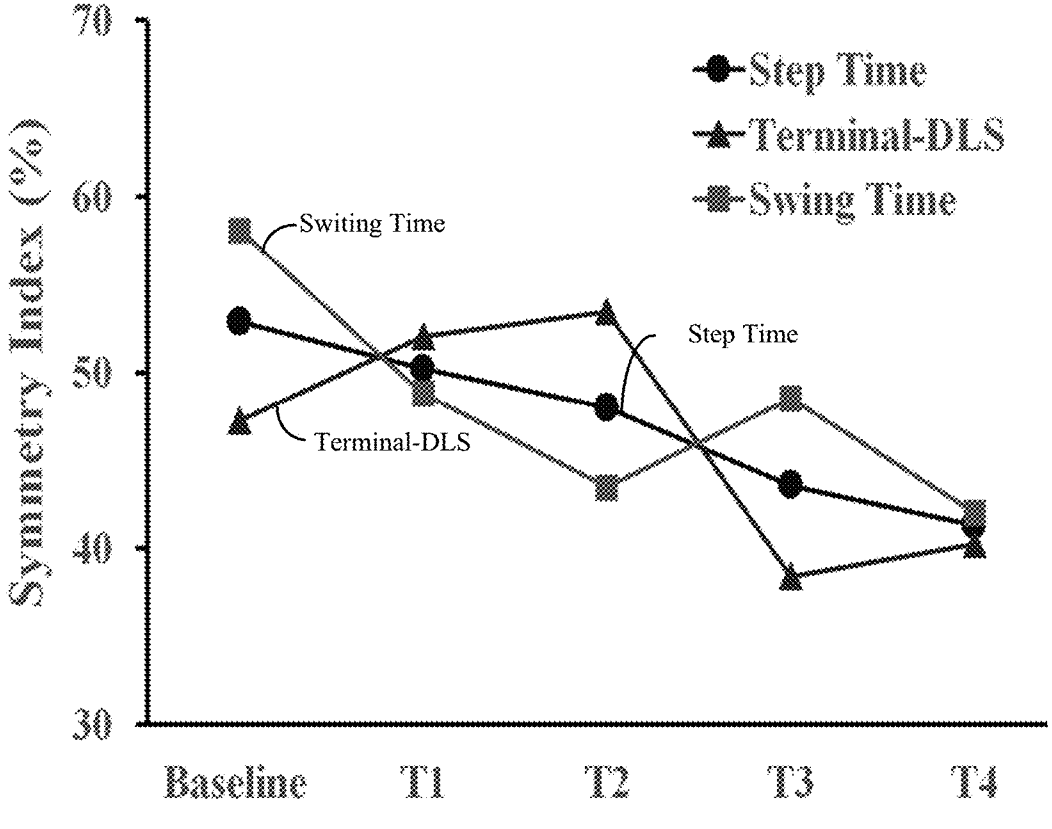
FIG. 11 shows changes in step time, swing time, and terminal double-limb support (DLS) symmetry across baseline and four A-RAC training sessions in a person with chronic stroke.

The subject with stroke demonstrated significant improvement in gait symmetry following the A-RAC gait training. The subject demonstrated a 12%, 16%, and 7% increase in step time, swing time, and terminal double-limb support (DLS) symmetry, respectively (FIG. 11). FIG. 11 shows changes in step time, swing time, and terminal double-limb support (DLS) symmetry across baseline and four A-RAC training sessions in a person with chronic stroke. The smaller the symmetry index, the better the temporal symmetry. Interestingly, the results show that the subject tried to walk more symmetrically by adjusting both swing time and terminal DLS time between the legs. His swing time symmetry and terminal DLS symmetry notably increased following the first two and last two training sessions. He also showed a 3-point increase in the FMA-LE motor function score in the lower extremity. Although the subject underwent only 4 training sessions, the changes in swing time symmetry and FMA-LE motor function following the A-RAC training is promising. In addition, the subject was complaint with A-RAC training throughout the training sessions. He stated that he relied on a cane far less than before during walking after training. His spouse also mentioned that he could walk around home much more comfortably, bearing more weight on the paretic leg.

In summary, the results of the preliminary studies show that A-RAC gait training could modify gait symmetry in neurologically intact individuals as well as in a person with chronic stroke. This suggests that gait training with A-RAC may have a high likelihood of succeeding for people with stroke.

3.3.2. Exemplary Study Design

This study is a randomized controlled trial. Subjects will be randomly divided into two different gait training programs: A-RAC and S-RAC.

3.3.2.1. Subjects

Eighteen individuals (60 to 90 years old), who have had a unilateral cerebral stroke at least 6 months prior to enrollment, will be recruited. Inclusion criteria for individuals post-stroke includes a) a unilateral cerebral stroke, b) no evidence of uncompensated hemianopsia, c) no evidence of a severe cognitive (greater than or equal to 18 in the Folstein Mini-Mental score) or language dysfunction that would interfere with understanding the instructions, d) a moderate to mild stroke (greater than 55 in the Fugl-Meyer motor assessment score), e) the ability to walk for at least 5 minutes, and f) the ability to hear auditory rhythms. An individual with stroke will be excluded if he/she has a) a history of a neurological disorder other than a stroke, such as Parkinson's disease and epilepsy, b) experienced a myocardial infarction within the last 90 days, or c) undergone any major surgery, such as total hip replacement, within the last 90 days.

3.3.2.2. Power Analysis for Sample Size

The primary outcome is the difference in step time symmetry index across three testing sessions (baseline, posttest, and follow-up) between the A-RAC and S-RAC gait training. The power calculation is based on a two-way repeated measures analysis of variance (ANOVA), using the results of a randomized controlled trial that investigated gait training with auditory cueing in stroke patients. The following assumptions are used for power calculation: (1) an average difference between A-RAC and S-RAC across three testing sessions is 28.9, (2) a standard deviation of the difference is 20.8 and (3) within-subject correlation coefficient of the step time gait symmetry is 0.5. A sample size of 16 (8 per group) will achieve a power of 88.5% to detect the difference of 28.9 between the A-RAC and S-RAC gait training with an effect size of 0.85 and a significance level of 0.05. Therefore, our proposed sample size of 18 subjects that considered 10% dropout rate is sufficient to confirm the significance of the study outcomes.

3.3.3. Exemplary Testing Procedure

An examiner (PI) and a research assistant will test the subjects' over-ground walking to measure gait symmetry a week before training (baseline), immediately after training (posttest), and 1 month after the completion of training (follow-up). The subjects' over-ground walking will be assessed using a suitable gait analysis system. In some examples, the gait analysis system may be the ProtoKinetics Zeno Walkway System (ProtoKinetics, Havertown, PA). For each test, the subjects will be asked to walk at their comfortable speed along the 26-foot long walkway. Each subject will have a practice trial and five actual trials of walking. Step time collected from the baseline test will be used to compute a ratio of auditory cueing that is applied to each foot during the adaptability test. Other gait variables (e.g., swing time, terminal double-limb support, step length, and estimated ground reaction forces) will be measured to monitor the gait symmetry change. Estimated ground reaction forces during the stance phase of walking will be assessed using the instrumented walkway system.

3.3.3.1. Exemplary Adaptability Test

The adaptability test will be performed at baseline and prior to each training session. A 5-minute baseline asymmetric audio file created from the baseline step time data will be uploaded into an examiner's smart phone and played to the subject during the test. The audio file consists of continuous cueing that plays "Right" and "Left" sounds at a ratio that graduation changes from the baseline step time asymmetry to a 2:1 (non-paretic:paretic) ratio. The ratio will be switched if the non-paretic leg's baseline step time is greater. The subject will then be asked to walk on an over ground walkway, following the auditory cues. The examiner will identify the time point when the subject fails to follow the asymmetric cues over three consecutive steps of a foot. The identified time point will be used for further correlation analysis. Subjects will be given a week break between the baseline test and training. The subject will wear a gait belt throughout the experiment. The examiner will walk slightly behind the subject for safety without interfering in the testing sessions. The literature reported that healthy people might have an asymmetrical gait pattern although the level is minimal (e.g., less than 2% symmetry index). Thus, in this proposed study, subjects with stroke who have less than 2% symmetry index of step time based on baseline test will be excluded from the study.

3.3.3.2. Exemplary Assessment of Lower Extremity Motor Function

A research physical therapist will examine the subjects' recovery of lower extremity motor function using the FMA.

The therapist will be blind to the training groups. FMA has excellent interrater and intrarater reliability, and is widely used as a valid measure of motor recovery after stroke. Modified Ashworth Scale will be also used to assess muscle tone (i.e., the resistance of muscle to passive stretching).

3.3.4. Exemplary Training Procedure for Gait Adaptation

Figure 12:
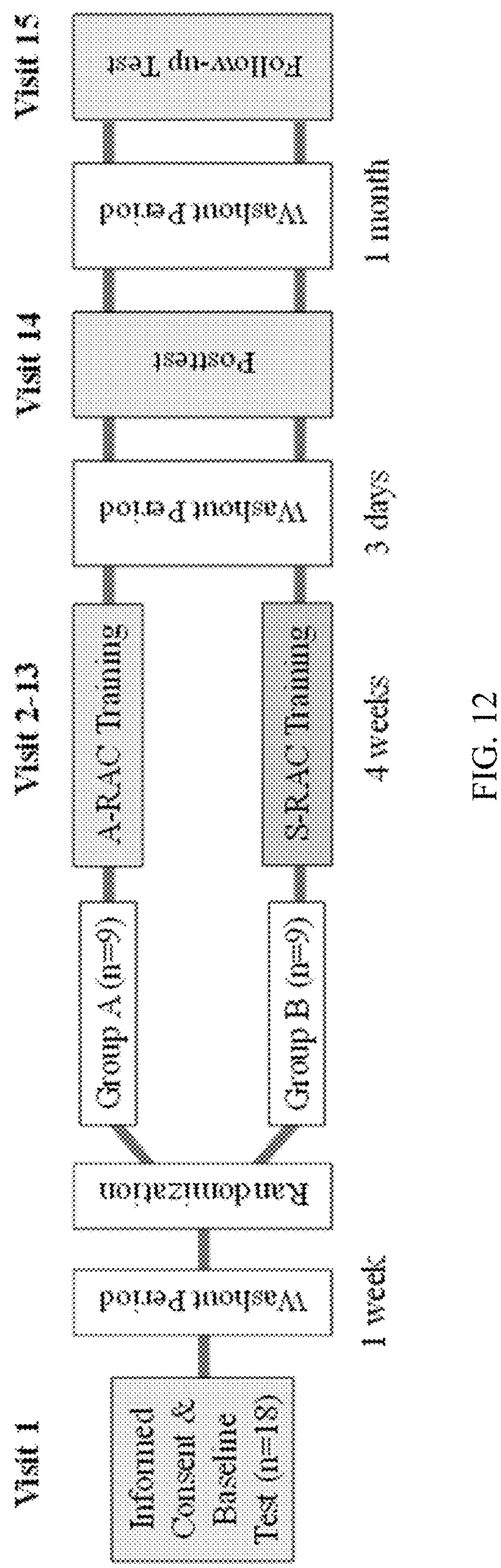
FIG. 12 shows an experimental procedure.

Eighteen subjects will be randomly divided into two groups (9 per group): A-RAC and S-RAC. Each group will undergo 12 sessions of gait training (30 minutes each) over 4 weeks (FIG. 12). FIG. 12 shows an experimental procedure for A-RAC group and S-RAC group. Each training session consists of a total of 30 minutes walking that includes six 5-minute bouts of over-ground walking with 2 minutes of rest between bouts. Each session will be performed under the guidance of an examiner (PI). The examiner will instruct the subjects how to perform the gait training session properly. The rhythmic cueing will contain A-RAC or S-RAC of "Right" and "Left" sounds during training. The subjects will be asked to walk around a 20-meter walkway, making best effort to take steps following the auditory cueing during walking. The subject's vital signs (i.e., heart rate, blood pressure, peripheral capillary oxygen saturation ($SpO_2$), and respiratory rate) will be recorded before and after each training bout. The subject's RPE will be also assessed using the Borg scale immediately following each training bout. The subject will be asked whether they feel any pain or discomfort in any part of their body throughout the training session. The subjects will be also asked to take a rest break if the Borg Scale exceeds 15 during training. If resting heart rate is >120 or <50 beats/min or resting $SpO_2$ is <88%, they will be instructed to discontinue the training for that day and report to the PI immediately. The PI and research staffs will determine whether the subject continues the rest of training sessions based on his/her medical condition.

For the A-RAC group, the adaptability test for training will be performed prior to each training session using the same procedure as described in 3.3.3.1. Adaptability Test. However, for the S-RAC group, the adaptability test for training will be performed using a 5-minute symmetric baseline audio file created from the average step time at baseline. The symmetric baseline audio file consists of continuous auditory cueing, containing "Right" and "Left" sounds from the baseline cadence to a 50% increase of the baseline cadence with a 1:1 ratio between the legs. The examiner will determine the time point when the subject fails to follow the symmetric cues over three consecutive steps of a foot. For both the A-RAC and S-RAC groups, a training audio file for each training session will be computed based on the identified time point and then uploaded into an examiner's smart phone. While turning on the training audio file, the examiner will walk behind the subject to make sure the subject is following the beats correctly. If the identified time point at the adaptability test of the following training session is earlier than that of the previous training session, the previous training audio file will be applied for the training session.

3.3.4.1. Exemplary Ratio of Auditory Cueing

Studies showed that 2:1 might be an ideal target ratio of asymmetrical perturbation for gait symmetry training. However, it is not feasible to apply a 2:1 ratio of auditory cueing to most stroke patients at the first training session due to the impairments of motor control, especially in the affected side. Thus, for the A-RAC training, as mentioned above, this proposed study will use a progressive training approach in which the asymmetric auditory cueing is gradually changed up to a 2:1 ratio between the non-paretic and paretic legs, respectively, based on the subject's progress. We presented how the ratio of asymmetric auditory cueing can be adjusted over the different training sessions in 3.3.1. Preliminary Study. Since the paretic leg in a stroke patient usually takes more prolonged steps than the non-paretic leg, the A-RAC training paradigm focuses on decreasing step time of the paretic leg and increasing step time of the non-paretic leg. For example, to create a 2:1 ratio, if the mean step time at baseline is 600 msec, the duration of auditory cueing for the non-paretic side is 800 msec ($600\times4/3$) and that for the paretic side is 400 msec ($600\times2/3$).

3.3.5. Exemplary Data Processing and Statistical Analysis

Subjects' temporal gait variables (e.g., step time, swing time, and terminal DLS) collected during over-ground walking tests will be processed using a suitable gait analysis software. In some examples the gait analysis software may be the ProtoKinetics Zeno Walkway analysis software. Other gait variables including step length and estimated ground reaction force will be also assessed. Symmetry indices (SI) of temporal gait variables will be calculated for further analysis to verify the hypotheses in this proposed study. For example, step time symmetry will be calculated as follows: SI (%)=[(paretic side−non-paretic side)/0.5×(paretic side+non-paretic side)]×100. In this case, a positive value indicates a prolonged step time of the paretic side. Zero value represents a perfect symmetry between the paretic and non-paretic sides. The FMA-LE motor function score will also be analyzed to identify the effects of A-RAC training on the lower limb motor function. In addition, how gender and the Modified Ashworth Scale can influence the changes in gait symmetry and FMA-LE motor function following gait training will be evaluated.

3.3.5.1. To Identify if 4 Weeks of A-RAC Gait Training can Increase Temporal Gait Symmetry and Motor Function of the Lower Extremity in People with Chronic Stroke Two-way repeated measures ANOVA with interaction effects will be conducted using two dependent variables (step time symmetry and FMA-LE motor function score). Two independent variables will be tested: training condition (A-RAC vs. S-RAC) and testing period (baseline, posttest, and one month follow-up). One main effect of training condition will compare how A-RAC and S-RAC affect step time symmetry (Hypothesis 1.1) and FMA-LE motor function (Hypothesis 1.2). A second main effect of testing period will evaluate whether gait training with auditory cueing improves step time symmetry and FMA-LE motor function in stroke patients. If the testing period shows statistical significance, a post hoc analysis will be performed using a paired t test with the Bonferroni correction. If the interaction between testing period and training condition is statistically significant, a post hoc analysis will determine which testing period(s) differed. All subjects will be analyzed using an intention-to-treat analysis. The level of significance (a) is set at 0.05. All statistical tests will be conducted using a suitable statistics software. In some example the software may be IBM SPSS Statistics.

3.3.5.2. To Compare the Effect of A-RAC Training on Gait Symmetry in Stroke Patients with High Gait Adaptability to A-RAC Training to Those with Low Gait Adaptability at Baseline Pearson correlation coefficient will be conducted to identify the relationship between gait adaptability at baseline (i.e., the time point when the subject fails to follow the asymmetric cues) and changes in step time symmetry across the three testing periods (Hypothesis 2). The significance level is set at 0.05.

3.3.5.3. Other Analyses

Spearman correlation coefficient will be conducted to examine the relationship between gender and changes in step time symmetry and FMA-LE motor function across the three testing periods as well as between the baseline Modified Ashworth Scale and changes in step time symmetry and FMA-LE motor function across the three testing periods.

3.4. Anticipated Results

Subjects undergoing A-RAC gait training will show significantly greater improvements in two primary measures (i.e., step time symmetry and FMA-LE motor function), compared to those who have S-RAC. This proposed feasibility study provides a foundation for both future in-clinic and home-based gait training studies for people with stroke.

4. Hardware Implementation

The concepts and methods described above can be implemented through a variety of hardware and software devices and systems, which can control or otherwise work in concert with various interventional therapy devices such as treadmills. In some embodiments, an electronic device can be added to or integrated with a treadmill or similar therapeutic device, to control speed and auditory cueing per the methods above. Such embodiments may also include one or more user interfaces, such as an interface for the patient undergoing treatment (e.g., a visual cue to match the auditory cue, or a dashboard to indicate current speed, time elapsed, distance, therapeutic goals, etc.) and an interface for a therapist or other individual who prescribes or supervises the therapy. In other embodiments, a separate device that is independent of a treadmill, such as a mobile device, tablet, or remote computer, can be utilized to provide the auditory cueing (e.g., through headphones or an ambient speaker, or another speaker via Bluetooth®) and/or connect to a treadmill to control speed of the treadmill in coordination with the asymmetric speed/cadence of auditory cueing.

Figure 13:
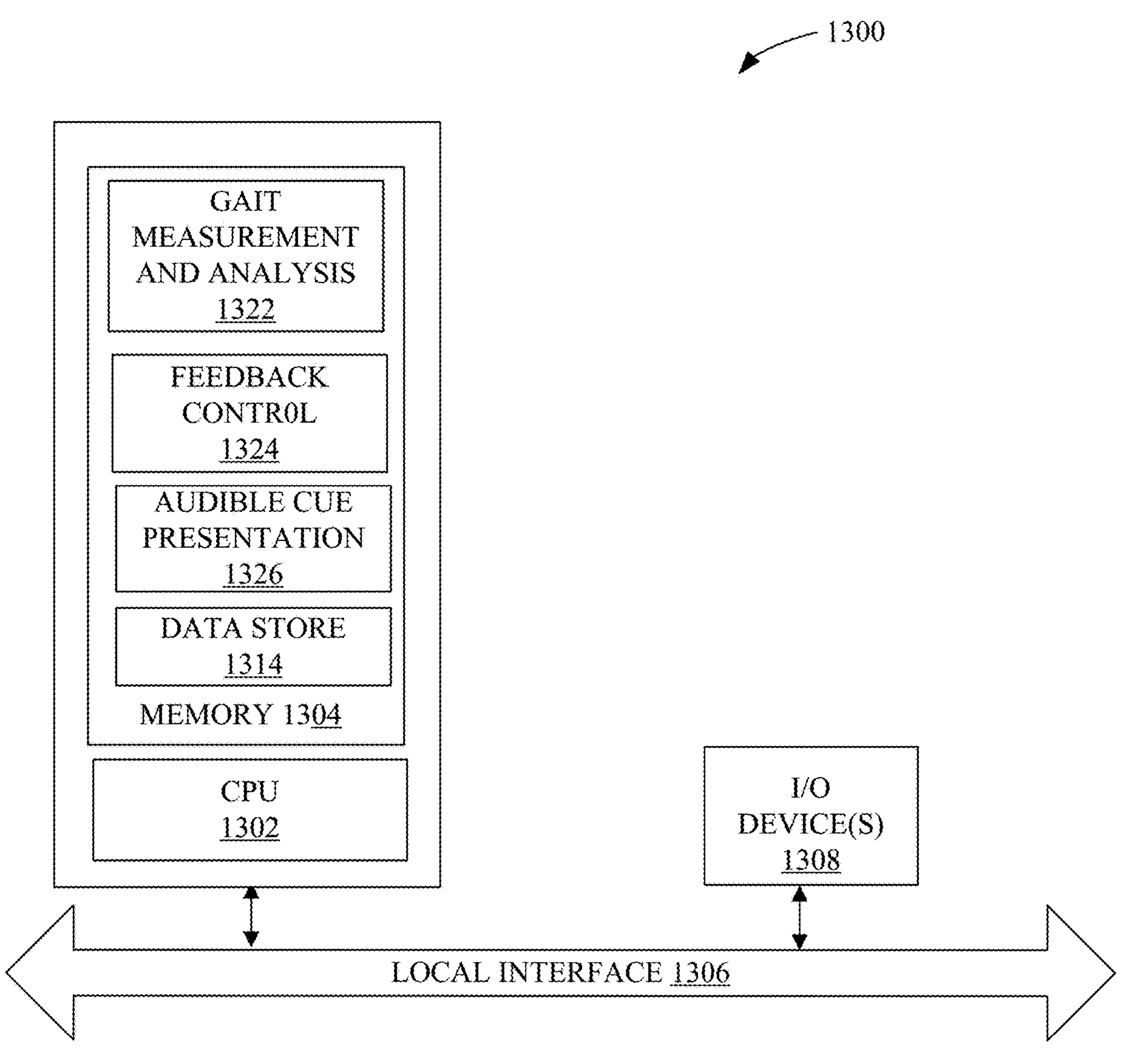
FIG. 13 depicts a schematic block diagram of an electronic device that can be used to implement various embodiments of the present disclosure.

FIG. 13 depicts a schematic block diagram of an electronic device 1300 that can be used to implement various embodiments of the present disclosure. This device can be integrated as part of the control system of a treadmill, or could be a separate mobile device or computer. An exemplary device 1300 includes at least one processor circuit, for example, having a processor 1302 and a memory 1304, both of which are coupled to a local interface 1306, and one or more input and output (I/O) devices 1308. The local interface 1306 may comprise, for example, a data bus with an accompanying address/control bus or other bus structure as can be appreciated. The CPU can perform various operations such as playing audio cue files, acquiring gait sensor data (e.g., spatial and temporal gait parameter data), analyzing the gait sensor data to obtain gait measurement values, measuring a first baseline step time for a first leg of an individual and a second baseline step time for a second leg of the individual, the first baseline step time being shorter than the second baseline step time, determining a first target step time for the first leg and a second target step time for the second leg, generating a series of auditory cues comprising a first cue, a second cue, and a third cue in series, adjusting the first target step time for the first leg and the second target step time such that the first target step time is longer than the second target step time, determining a target step speed based on the first target step time and the second target step time, and any of the various operations described herein. In some examples, the computing device 1300 may be included in a split-belt treadmill, a mobile device.

Stored in the memory 1304 are both data and several components that are executable by the processor 1302. In particular, stored in the memory 1304 and executable by the processor 1302 are code for implementing gait measurement and analysis 1322, feedback control 1324, or presentation of audible cues 1326 in accordance with embodiments of the present disclosure. Also stored in the memory 1304 may be a data store 1314 and other data. The data store 1314 can include an audio cue file database and potentially other data related to the computations performed by the processor 1302. In addition, an operating system may be stored in the memory 1304 and executable by the processor 1302. The I/O devices 1308 may include input devices, for example but not limited to, a keyboard, touchscreen, mouse, one or more cameras and/or sensors, etc. For example, the sensors may include optical means (camera or depth/distance sensor), a wearable motion sensor, a wearable device (a simple phone in a pocket would probably be enough), a vibration/strike sensor integrated in a shoe or into a treadmill, a force plate, a motion capture camera, or any other suitable sensor. In further examples, a treadmill may include controllable tension on lateral/foot pulls, which are controllable by the computing device 1300. Furthermore, the I/O devices 1308 may also include output devices, for example but not limited to, speaker, earbuds, audio output port, a printer, display, Bluetooth output module, etc. In various embodiments, the electronic device 1300 may be in the form of a smartphone having smartphone capabilities including making phone calls, text messaging, and internet browsing capabilities.

Embodiments of the present disclosure can be implemented in hardware, software, firmware, or a combination thereof. In an exemplary embodiment, measurement/feedback/audio presentation logic or functionality is implemented in software or firmware that is stored in a memory and that is executed by a suitable instruction execution system. If implemented in hardware, as in an alternative embodiment, categorization/assessment logic or functionality can be implemented with any or a combination of the following technologies, which are all well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Figure 14:
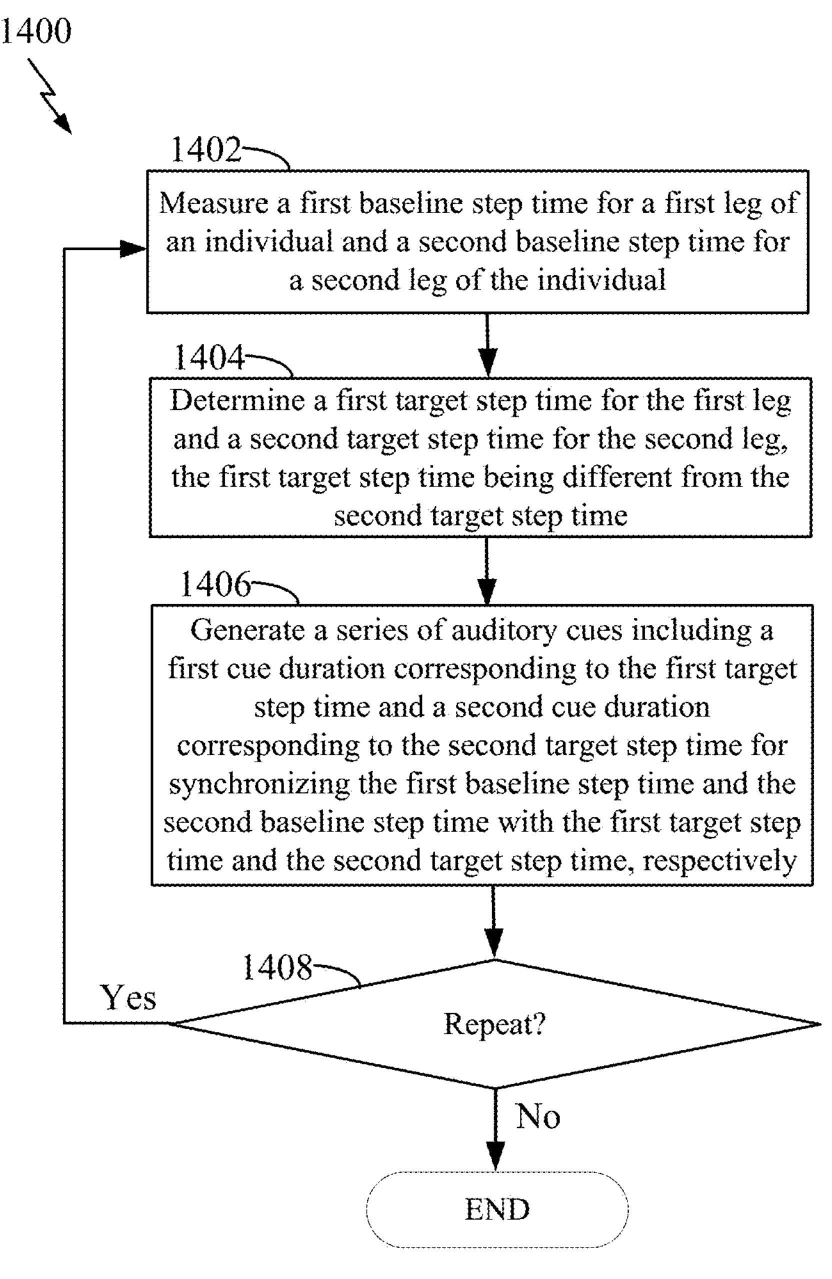
FIG. 14 is a flow chart illustrating an exemplary process 1400 for modifying and assessing gait asymmetry in accordance with some aspects of the present disclosure.

FIG. 14 is a flow chart illustrating an exemplary process 1400 for modifying and assessing gait asymmetry in accordance with certain aspects of the present disclosure. As described below, a particular implementation may omit some or all illustrated features, and may not require some illustrated features to implement all embodiments. In some examples, the apparatus or computer device 1300 illustrated in FIG. 13 may be configured to carry out the process 1400.

In some examples, any suitable apparatus or means for carrying out the functions or algorithm described below may carry out the process 1400.

At block 1402, the method may measure a first baseline step time for a first leg of an individual and a second baseline step time for a second leg of the individual. Here, the first baseline step time may be shorter than the second baseline step time or vice versa. In some examples, the first leg may indicate a paretic or an amputated leg while the second leg may indicate a non-paretic or a non-amputated leg. However, the methods of the present disclosure are not limited to such indications. In other examples, the first leg could be a non-paretic or a non-amputated leg while the second leg could be a paretic or an amputated leg. The first baseline step time may be the time between a first ground contact of the first leg and a second ground contact of the second leg while the second baseline step time may be the time between the second ground contact of the second leg and the subsequent ground contact of the first leg. In some examples, the step time is a time for a person moves a step length. The step length may be the distance between heel locations upon heel-strike. The definition is used for the real-time algorithm. Thus, as the person walks, the step time and the step length can be recorded upon each heel strike as heel Z coordinate location minus contralateral heel Z coordinate location. In some examples, the first baseline step time may be a first average step time of a plurality of first step times of the first leg for a predetermined period of time. The second baseline step time may be a second average step time of a plurality of second step times of the second leg for the predetermined period of time.

At block 1404, the method may determine a first target step time for the first leg and a second target step time for the second leg. In some examples, the first target step time may be different from the second target step time at a first time. In some examples, the first target step time is determined to be between the first baseline step time and the second baseline step time while the second target step time is determined to be between the first baseline step time and the second baseline step time. In further examples, the first and second target step times may gradually change. For example, at first, the first target step time is shorter than the second target step time, and later the second target step time is shorter than the first target step time. Thus, in further examples, the method may adjust the first target step time for the first leg and the second target step time such that the first target step time is longer than the second target step time. In further examples, the method may adjust the first target step time and the second target step time at a second time such that the first target step time is equal to the second target step time. In some scenarios, a ratio of the first target step time to the second target step time is equal to or less than 5. That is, the ratio of the first target step time to the second target step time may be any ratio between 1:5 and 5:1.

In further examples, the method may determine the first cue duration and the second cue duration based on the first target step time and the second target step time, respectively. In some examples, the first cue duration increases from the first baseline step time to the first target step time, and the second cue duration decreases from the second baseline step time to the second target step time. In other examples, the first cue duration decreases from the first baseline step time to the first target step time, and the second cue duration increases from the first baseline step time to the second target step time.

At block 1406, the method may generate a series of auditory cues comprising a first cue duration corresponding to the first target step time and a second cue duration corresponding to the second target step time for synchronizing the first basic step time and the second basic step time with the first target step time and the second target step time, respectively. Here, the first cue duration may be the duration between a first auditory cue and a second auditory cue while the second cue duration may be the duration between the second auditory cue and the subsequent first auditory cue. Thus, a person who follows the method can modify his or her baseline step time to synchronize the series of auditory cues. In some examples, to apply the ratio of auditory cueing between the legs during training, an audio file including "Right" and "Left" sounds can be created using a suitable software corresponding to the first and second auditory cue durations.

In further examples, the method may determine adaptability of the individual to follow the series of auditory cues. The determination may be by increasing the first cue duration and decreasing the second cue duration on subsequent steps, measuring a third baseline step time for the first leg and a fourth baseline step time for the second leg, comparing the increased first cue duration to the third measured step time and the decreased second cue duration to the fourth measured step time, and determining a maximum asymmetry based on a result of the comparing the increased first cue duration and the decreased second cue duration, the maximum asymmetry that the individual follows.

At block 1408, the method may determine repeating the processes 1402-1406. In some examples, measuring the baseline step times, determining and adjusting the target step times, and generating a series of auditory cues based on the baseline step times and the target step times are performed in a real-time basis. Thus, a person who follow the method can modify their gait pattern in a real-time basis such that the target step times constantly changes to modify the baseline step times to improve the person's asymmetric gait pattern.

In other alternative implementations of the above-referenced methods, a system that implements the above methods may be entirely automated via an electronic device (either integrated in a physical therapy treadmill or a separate device). For example, a software application operating on a mobile device such as a smartphone can automate the process of measuring gait asymmetry, determining appropriate auditory cueing cadence for each leg, and setting a treadmill speed in coordination with the pace of cueing. In such an embodiment, a sensor associated with the mobile device (such as an accelerometer or other sensor) can measure gait cadence for each leg. The software can then determine an appropriate asymmetric cueing, per the methods and techniques described above. The mobile device can then either directly control a treadmill (e.g., via a Bluetooth connection) or provide an instruction to a user to control a treadmill to adjust to a given speed appropriate for the user (based on a user history, user age, or user preference), then begin playing the asynchronous auditory cueing to the user. While the user is walking on the treadmill per the cueing, the device can continue to measure gait asymmetry. Real time adjustments to treadmill speed and cueing cadence per leg can then be made. For example, if the user is unable to keep up with the current cueing cadence, then several changes can be made as described above: the cueing for the leg that tends to take longer steps can be made faster, the cueing for the leg that tends to take shorter steps can be made longer, or the amount of intervention for either leg can be reduced (e.g., to adjust for user fatigue). As another example, the treadmill speed could be gradually increased during a therapy session (or session-by-session according to data stored regarding the user's profile), or the amount of therapeutic intervention (e.g., the degree of asynchronicity, volume or relative volume of cues per leg can be increased/decreased) could be increased. In other implementations, the mobile device can be operated by or supervised by a therapist.

In further embodiments, an optical camera watches a user's gait and then signals a mobile device of a therapist to give real-time assessment and allow the therapist to adjust settings including the speed of treadmill and/or the auditory cue duration of each leg.

It should be emphasized that the above-described embodiments are merely possible examples of implementations, merely set forth for a clear understanding of the principles of the present disclosure. Many variations and modifications may be made to the above-described embodiment(s) without departing substantially from the principles of the present disclosure. All such modifications and variations are intended to be included herein within the scope of this disclosure.

The advantages set forth above, and those made apparent from the foregoing description, are efficiently attained. Since certain changes may be made in the above construction without departing from the scope of the present disclosure, it is intended that all matters contained in the foregoing description or shown in the accompanying drawings shall be interpreted as illustrative and not in a limiting sense.

It is also to be understood that the following claims are intended to cover all of the generic and specific features herein described, and all statements of the scope of the present disclosure that, as a matter of language, might be said to fall therebetween.

The invention claimed is:

1. A method for treating gait asymmetry of a patient having asymmetric gait impairment comprising:

measuring a first baseline step time for a first leg of the patient and a second baseline step time for a second leg of the patient, the first baseline step time being shorter than the second baseline step time;

determining an asymmetrical rhythm tolerance for the patient;

determining a first target step time for the first leg and a second target step time for the second leg, the first target step time being different from the second target step time at a first time;

generating a series of auditory cues based on the asymmetrical rhythm tolerance, the series of auditory cues comprising interleaved first cues for the first leg and second cues for the second leg and having:

a first cue cadence based on the first baseline step time and the first target step time, and a second cue cadence, different from the first cue cadence, based on the second baseline step time and the second target step time;

administering the series of auditory cues to the patient;

measuring patient gait data responsive to the patient walking in accordance with the series of auditory cues; and monitoring the patient gait data.

2. The method of claim 1, further comprising:

adjusting the first target step time and the second target step time at a second time such that the first target step time is equal to the second target step time.

3. The method of claim 1, wherein the first target step time is determined to be between the first baseline step time and the second baseline step time, and wherein the second target step time is determined to be between the first baseline step time and the second baseline step time.

4. The method of claim 3, wherein the first target step time is shorter than the second target step time.

5. The method of claim 3, wherein the second target step time is shorter than the first target step time.

6. The method of claim 1, further comprising:

adjusting the first target step time for the first leg and the second target step time such that the first target step time is equal to or longer than the second target step time.

7. The method of claim 6, wherein a ratio of the first target step time to the second target step time is equal to or less than 5.

8. The method of claim 1, further comprising:

increasing the first cue cadence from a first earlier value based on the first baseline step time to a first later value based on the first target step time, and decreasing the second cue cadence from a second earlier value based on the second baseline step time to a second later value based on the second target step time; or decreasing the first cue cadence from the first earlier value based on the first baseline step time to the first later value based on the first target step time, and increasing the second cue cadence from the second earlier value based on the second baseline step time to the second later value based on the second target step time.

9. The method of claim 1, wherein the first baseline step time is a first average step time of a plurality of first step times of the first leg for a predetermined period of time, and wherein the second baseline step time is a second average step time of a plurality of second step times of the second leg for the predetermined period of time.

10. The method of claim 1, further comprising:

determining adaptability of the patient to follow the series of auditory cues by:

decreasing the first cue cadence and increasing the second cue cadence on subsequent steps, measuring a third baseline step time for the first leg and a fourth baseline step time for the second leg, comparing the decreased first cue cadence to the third measured step time and the increased second cue cadence to the fourth measured step time, and determining a maximum asymmetry that the patient follows based on a result of the comparing the decreased first cue cadence to the third measured step time and the increased second cue cadence to the fourth measured step time; and determining the asymmetrical rhythm tolerance based on the maximum asymmetry.

11. The method of claim 1, further comprising:

determining rhythmic synchronization capabilities based on the monitored data and the series of audio cues; and increasing or decreasing the first cue cadence or the second cue cadence of the series of audio cues responsive to the rhythmic synchronization capabilities.

12. The method of claim 1, further comprising generating the series of audio cues based on a session-specific step-time ratio.

13. The method of claim 12, wherein the asymmetrical rhythm tolerance comprises a current session-specific asymmetrical rhythm tolerance, and the method further comprising determining the session-specific step-time ratio based on a prior session-specific asymmetrical rhythm tolerance and the current session-specific asymmetrical rhythm tolerance.

14. An apparatus for treating gait asymmetry of a patient having asymmetric gait impairment, comprising:

a processor; and a memory communicatively coupled to the processor, wherein the processor and the memory are configured to:

measure a first baseline step time for a first leg of an the patient and a second baseline step time for a second leg of the patient, the first baseline step time being shorter than the second baseline step time;

determine an asymmetrical rhythm tolerance for the patient;

determine a first target step time for the first leg and a second target step time for the second leg, the first target step time being different from the second target step time at a first time;

generate a series of auditory cues based on the asymmetrical rhythm tolerance, the series of auditory cues comprising interleaved first cues for the first leg and second cues for the second leg and having:

a first cue cadence based on the first baseline step time and the first target step time, and a second cue cadence, different from the first cue cadence, based on the second baseline step time and the second target step time;

administer the series of auditory cues to the patient;

measure patient gait data responsive to the patient walking in accordance with the series of auditory cues; and monitor the patient gait data.

15. The apparatus of claim 14, wherein the processor and the memory are further configured to:

adjust the first target step time and the second target step time at a second time such that the first target step time is equal to the second target step time.

16. The apparatus of claim 14, wherein the first target step time is determined to be between the first baseline step time and the second baseline step time, and wherein the second target step time is determined to be between the first baseline step time and the second baseline step time.

17. The apparatus of claim 16, wherein the first target step time is shorter than the second target step time.

18. The apparatus of claim 16, wherein the second target step time is shorter than the first target step time.

19. The apparatus of claim 14, wherein the processor and the memory are further configured to:

adjust the first target step time for the first leg and the second target step time such that the first target step time is longer than the second target step time.

20. The apparatus of claim 19, wherein a ratio of the first target step time to the second target step time is equal to or less than 5.

21. The apparatus of claim 14, wherein the first cue cadence decreases from a first earlier value based on the first baseline step time to a first later value based on the first target step time, and the second cue cadence increases from a second earlier value based on the second baseline step time to a second later value based on the second target step time, or wherein the first cue cadence increases from the first earlier value based on the first baseline step time to the first later value based on the first target step time, and the second cue cadence decreases from the second earlier value based on the second baseline step time to the second later value based on the second target step time.

22. The apparatus of claim 14, wherein the first baseline step time is a first average step time of a plurality of first step times of the first leg for a predetermined period of time, and wherein the second baseline step time is a second average step time of a plurality of second step times of the second leg for the predetermined period of time.

23. The apparatus of claim 14, wherein the processor and the memory are further configured to:

determine adaptability of the patient to follow the series of auditory cues by:

decreasing the first cue cadence and increasing the second cue cadence on subsequent steps, measuring a third baseline step time for the first leg and a fourth baseline step time for the second leg, comparing the decreased first cue cadence to the third measured step time and the increased second cue cadence to the fourth measured step time, and determining a maximum asymmetry that the patient follows based on a result of the comparing the decreased first cue cadence to the third measured step time and the increased second cue cadence to the fourth measured step time; and determine the asymmetrical rhythm tolerance based on the adaptability.

24. The apparatus of claim 14, wherein the processor and the memory are further configured to:

determine rhythmic synchronization capabilities based on the monitored data and the series of audio cues; and increase or decrease the first cue cadence or the second cue cadence of the series of audio cues responsive to the rhythmic synchronization capabilities.

25. The apparatus of claim 14, wherein the processor and the memory are further configured to generate the series of audio cues based on a session-specific step-time ratio.

26. The apparatus of claim 25, wherein the asymmetrical rhythm tolerance comprises a current session-specific asymmetrical rhythm tolerance, and wherein processor and the memory are further configured to determine the session-specific step-time ratio based on a prior session-specific asymmetrical rhythm tolerance and the current session-specific asymmetrical rhythm tolerance.

* * * * *